United States Patent
Bihlmaier et al.

(10) Patent No.: US 11,291,749 B2
(45) Date of Patent: Apr. 5, 2022

(54) ANTIMICROBIAL INSERTS FOR MEDICAL DEVICES

(71) Applicant: Becton, Dickinson and Company, Franklin Lakes, NJ (US)

(72) Inventors: Bryan Fred Bihlmaier, Provo, UT (US); Weston F. Harding, Lehi, UT (US); Janice Lin, San Jose, CA (US); Huibin Liu, Cupertino, CA (US); Siddarth K. Shevgoor, Mission Viejo, CA (US); Jonathan Karl Burkholz, Salt Lake City, UT (US); Yiping Ma, Layton, UT (US); Ming Zhou, Buffalo Grove, IL (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/009,473

(22) Filed: Sep. 1, 2020

(65) Prior Publication Data
US 2021/0023277 A1    Jan. 28, 2021

Related U.S. Application Data

(60) Division of application No. 14/606,833, filed on Jan. 27, 2015, now Pat. No. 10,792,399, which is a (Continued)

(51) Int. Cl.
*A61L 29/16* (2006.01)
*A61L 29/12* (2006.01)
(Continued)

(52) U.S. Cl.
CPC .............. *A61L 29/16* (2013.01); *A61L 29/06* (2013.01); *A61L 29/126* (2013.01); *A61L 29/14* (2013.01);
(Continued)

(58) Field of Classification Search
None
See application file for complete search history.

(56) References Cited

U.S. PATENT DOCUMENTS

| 4,540,025 A | 9/1985 | Ledeen et al. |
| 4,932,948 A | 6/1990 | Kernes et al. |
| (Continued) | | |

FOREIGN PATENT DOCUMENTS

| CN | 1242781 | 1/2000 |
| CN | 102472401 | 5/2012 |
| (Continued) | | |

OTHER PUBLICATIONS

Merriam Webster (available online at https://www.merriam-webster.com/dictionary/proximal, accessed Jul. 23, 2019) (Year 2019).

*Primary Examiner* — Dominic Lazaro
(74) *Attorney, Agent, or Firm* — Kirton McConkie; Whitney Blair; Kevin Stinger

(57) ABSTRACT

Inserts can be formed with elution characteristics to cause the inserts to elute an antimicrobial agent when subject to a fluid within a medical device. An insert can be formed with a desired geometry to allow the insert to be compression fit within a medical device to prevent the insert from moving or becoming dislodged once inserted into the medical device. The material may also be hygroscopic so that the insert swells when subject to a fluid thereby enhancing the compression fit of the device within the medical device. In some cases, the material can be reinforced using an internal structure. Inserts can be formed in many ways including by casting, thermoforming, or extrusion. In some cases, the inserts can be formed using a peel-away sleeve or material. The peel-away sleeves can be formed of a non-sticky material which facilitates removal of the inserts once the inserts have cured.

4 Claims, 22 Drawing Sheets

Related U.S. Application Data continuation-in-part of application No. 14/185,831, filed on Feb. 20, 2014, now Pat. No. 10,792,398.

(51) Int. Cl.
  *A61M 31/00* (2006.01)
  *A61L 29/14* (2006.01)
  *A61L 29/06* (2006.01)

(52) U.S. Cl.
  CPC ........ *A61M 31/00* (2013.01); *A61L 2300/206* (2013.01); *A61L 2300/404* (2013.01); *A61L 2300/602* (2013.01)

(56) References Cited

U.S. PATENT DOCUMENTS

| | | |
|---|---|---|
| 5,046,528 A | 9/1991 | Manska |
| 5,135,026 A | 8/1992 | Manska |
| 5,203,775 A | 4/1993 | Frank et al. |
| 5,354,267 A | 10/1994 | Niermann et al. |
| 5,680,889 A | 10/1997 | Boger |
| 6,171,287 B1 | 1/2001 | Lynn et al. |
| 6,706,022 B1 | 3/2004 | Leinsing et al. |
| 7,033,339 B1 | 4/2006 | Lynn |
| 7,184,825 B2 | 2/2007 | Leinsing et al. |
| 7,232,428 B1 | 6/2007 | Inukai et al. |
| 7,771,383 B2 | 8/2010 | Truitt et al. |
| 8,048,034 B2 | 11/2011 | Eversull et al. |
| 8,591,471 B1 | 11/2013 | Marble |
| 8,715,222 B2 | 5/2014 | Truitt et al. |
| 10,149,971 B2 | 12/2018 | Liu et al. |
| 2003/0199835 A1 | 10/2003 | Leinsing et al. |
| 2004/0013703 A1 | 1/2004 | Ralph et al. |
| 2004/0089834 A1 | 5/2004 | Aoshima et al. |
| 2006/0016496 A1 | 1/2006 | Shane |
| 2006/0089603 A1 | 4/2006 | Truitt et al. |
| 2007/0083188 A1 | 4/2007 | Grandt et al. |
| 2007/0119968 A1 | 5/2007 | Collins et al. |
| 2007/0287953 A1 | 12/2007 | Ziv et al. |
| 2008/0161763 A1 | 7/2008 | Harding et al. |
| 2008/0194707 A1 | 8/2008 | Potter |
| 2008/0195031 A1 | 8/2008 | Kitani et al. |
| 2008/0215021 A1 | 9/2008 | Cisko Jr et al. |
| 2009/0182309 A1 | 7/2009 | Muffly |
| 2010/0106102 A1 | 4/2010 | Ziebol et al. |
| 2010/0106103 A1 | 4/2010 | Ziebol et al. |
| 2010/0135949 A1 | 6/2010 | Ou-Yang |
| 2011/0257606 A1 | 10/2011 | Truitt et al. |
| 2012/0083750 A1 | 4/2012 | Sansoucy |
| 2012/0103448 A1 | 5/2012 | Hopf et al. |
| 2013/0012915 A1 | 1/2013 | Hopf et al. |
| 2013/0274686 A1 | 10/2013 | Ziebol et al. |
| 2014/0155844 A1 | 6/2014 | Isch et al. |
| 2014/0174578 A1 | 6/2014 | Bonnal et al. |
| 2014/0228466 A1 | 8/2014 | Lin et al. |
| 2014/0323970 A1 | 10/2014 | Duncan |
| 2015/0126699 A1 | 5/2015 | Yarrison et al. |
| 2015/0231307 A1 | 8/2015 | Shevgoor et al. |
| 2015/0231309 A1 | 8/2015 | Bihlmaier et al. |
| 2015/0306370 A1 | 10/2015 | Liu et al. |
| 2016/0008569 A1 | 1/2016 | Harding |
| 2016/0213911 A1 | 7/2016 | Liu et al. |

FOREIGN PATENT DOCUMENTS

| | | | |
|---|---|---|---|
| CN | 103013094 | 4/2013 | |
| DE | 4328095 | 2/1995 | |
| DE | 19728562 | 2/1999 | |
| DE | 102009050590 | 4/2011 | |
| EP | 0166375 | 1/1986 | |
| EP | 0410898 | 1/1991 | |
| EP | 1234596 | 8/2002 | |
| FR | 2791114 | 7/2002 | |
| GB | 1249484 | 10/1971 | |
| GB | 1262428 | 2/1972 | |
| JP | 63-020344 | 1/1988 | |
| JP | 02-234767 | 9/1990 | |
| JP | 03-029664 | 2/1991 | |
| JP | H08-141088 | 6/1996 | |
| JP | H08-508421 | 9/1996 | |
| JP | 08-280788 | 10/1996 | |
| JP | H11-70163 | 3/1999 | |
| JP | 2005530547 | 10/2005 | |
| JP | 2008-511371 | 4/2008 | |
| JP | 2008-517653 | 5/2008 | |
| JP | 2010-029381 | 2/2010 | |
| JP | 2010-179031 | 8/2010 | |
| JP | 2012-075901 | 4/2012 | |
| JP | 2012-523300 | 10/2012 | |
| JP | 2017513633 | 6/2017 | |
| JP | 2019155182 | 9/2019 | |
| WO | 94/22522 | 10/1994 | |
| WO | WO-9422522 A1 * | 10/1994 | ......... A61M 39/162 |
| WO | 97/35634 | 10/1997 | |
| WO | 2006/077951 | 7/2006 | |
| WO | 2011/006934 | 1/2011 | |
| WO | 2014/031774 | 2/2014 | |
| WO | 2015/126699 | 8/2015 | |
| WO | 2015/164130 | 10/2015 | |
| WO | 2015/164134 | 10/2015 | |

\* cited by examiner

ANTIMICROBIAL INSERTS FOR MEDICAL DEVICES

RELATED APPLICATIONS

This application is a divisional of U.S. patent application Ser. No. 14/606,833, filed Jan. 27, 2015, and titled ANTIMICROBIAL INSERTS FOR MEDICAL DEVICES, which is a continuation-in-part of U.S. patent application Ser. No. 14/185,831, filed Feb. 20, 2014 and titled ANTIMICROBIAL INSERTS FOR MEDICAL DEVICES, which is incorporated herein in its entirety.

BACKGROUND OF THE INVENTION

The present invention relates generally to inserts for medical devices that are configured to elute an antimicrobial agent. The inserts of the present invention can be particularly beneficial when used within one or more components of an infusion system.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheter-related bloodstream infections are caused by the colonization of microorganisms in patients with intravascular catheters and I.V. access devices. These infections are an important cause of illness and excess medical costs. More importantly, these infections often result in patient deaths.

Many techniques have been employed to reduce the risk of infection from a catheter or other intravenous device. For example, catheters have been designed that employ an antimicrobial lubricant or an antimicrobial coating on an inner or outer surface of the catheter. Similarly, antimicrobial lubricants or coatings have been applied to the surfaces of other components of a catheter assembly, components attached to the catheter assembly, or other medical devices which may come in direct contact with the patient's vasculature or in contact with a fluid that may enter the patient's vasculature. Further, some devices or components are made of a material that is impregnated with an antimicrobial agent.

Although these techniques have been beneficial, there are various drawbacks that limit their usefulness. For example, it can be difficult and/or expensive to apply an antimicrobial coating or lubricant to the complex internal and external geometries of many devices or components. Also, some devices or components are preferably made of a material that is not suitable for the application of an antimicrobial coating or that cannot be impregnated with an antimicrobial agent. Because of such difficulties, the current techniques for providing antimicrobial protection are oftentimes not used or, if used, are not adequately applied to provide maximum antimicrobial protection.

BRIEF SUMMARY OF THE INVENTION

The present invention extends to inserts for medical devices. The inserts are manufactured of a material that includes an antimicrobial agent and that has elution characteristics so that the antimicrobial agent is eluted from the material at a desired rate to provide antimicrobial protection to a medical device in which the insert is contained. An insert can be formed with a desired geometry to allow the insert to be compression fit within a medical device to prevent the insert from moving or becoming dislodged once inserted into the medical device. The material may also be hygroscopic so that the insert swells when subject to a fluid thereby enhancing the compression fit of the device within the medical device. In some cases, the material can be reinforced using an internal structure and/or an adhesive.

The inserts of the present invention can be used within a variety of medical devices to provide a desired level of antimicrobial protection to the medical devices. An insert can be designed to have a surface area that is sufficient for the volume of the location in which the insert is contained so that a sufficient amount of antimicrobial agent is eluted to disinfect the fluid within the area within a desired amount of time. Examples of medical devices or components in which the inserts of the present invention can be used include ports, stop cocks, male luers, female luers, IV sets, needleless connectors, respirators, catheters, devices for fluid infusion to the body or aspiration from the body, surgical instruments etc.

The inserts of the present invention can be manufactured in various ways. For example, the inserts can be formed in a desired geometry by casting, thermoforming, or extrusion. In some cases, the inserts can be formed using a peel-away sleeve. The peel-away sleeves can be formed of a non-sticky material which facilitates removal of the inserts once the inserts have cured.

In one embodiment, the present invention is implemented as an inset for a medical device. The insert comprises a base material having elution characteristics, and an antimicrobial agent contained within the base material so that the antimicrobial agent is eluted from the base material when the base material is exposed to or comes in contact with a fluid.

In some embodiments, the base material comprises a hygroscopic material that swells upon absorbing a fluid.

In some embodiments, the insert is bonded to a surface of the medical device using a curable adhesive.

In some embodiments, the insert is mechanically fastened to the medical device using features such as threads, snap-fits etc.

In some embodiments, the insert is made of a hydrophilic material to facilitate elution of a water soluble antimicrobial agent where the base material comprises a hydrophilic polymer such as urethane acrylate or a polyurethane polymer.

In some embodiments, the antimicrobial agent comprises between 0.1% and 40% w/w of the insert.

In some embodiments, the insert is formed by curing the base material containing the antimicrobial agent in a desired form. In some embodiments, the form comprises a tube shape or a rod shape. In some embodiments, the tube shape has an outer diameter that is equal to or larger than an inner diameter of a lumen of a medical device within which the insert will be placed.

In some embodiments, the insert is placed within a catheter adapter having a septum, wherein the insert secures the septum in place.

In some embodiments, the insert is formed within a peel-away sleeve. In some embodiments, the peel-away sleeve comprises one of: polyolefin; fluoropolymer; polyvinyl chloride; or ethylene vinyl acetate. In some embodiments, the insert is formed within a mold that is lined with one or more peel-away sheets.

In some embodiments, the insert comprises a reinforcing substructure contained within the base material.

In another embodiment, the present invention is implemented as a medical device comprising an insert that elutes an antimicrobial agent. The insert comprises a base material having elution characteristics, and an antimicrobial agent contained within the base material so that the antimicrobial agent is eluted from the base material when the base material is exposed to a fluid.

In some embodiments, the insert comprises a lumen through which fluid passes within the medical device.

In some embodiments, the insert attaches to and extends from a first medical device such that the insert is configured to contact and/or be inserted within a second medical device when the two medical devices are connected. As such, the eluted antimicrobial agent from the insert provides antimicrobial protection to both of the medical devices.

In another embodiment, the present invention is implemented as a method for forming an insert for a medical device. A base material having elution characteristics is combined with an antimicrobial agent to form a base material matrix. The base material matrix is then formed into an insert that is sized and shaped to be inserted and contained within a medical device.

In some embodiments, the base material matrix is formed into the insert using UV curing, heat curing, or heat forming.

In some embodiments, the insert contains materials that at least partially dissolve into the fluid resulting in partial or even complete dissolution of the insert upon use.

In some embodiments, they insert comprises a matrix, such as a cross-linked polymer or a ceramic, that does not dissolve in to the fluid while the antimicrobial agent contained within the matrix at least partially dissolves.

In some embodiments, forming the base material matrix into the insert comprises placing the base material matrix within a peel-away material.

In some embodiments, the method includes placing the insert within the medical device such that the insert is exposed to a fluid to cause the antimicrobial agent to elute from the insert into the fluid.

In some embodiments, the insert may serve a mechanical function such as a support feature for other components of the medical device or a fluid conduit or a mating feature to another device or component.

Some implementations of the present invention further provide antimicrobial luer stoppers. Antimicrobial strips and antimicrobial annular inserts are also provided for various medical devices, such as for insertion within a side port of a catheter adapter. Various embodiments of the present invention further include a medical device having an antimicrobial side port that is coupled to the medical device via an adhesive and/or a weld.

Some implementations of the instant invention further provide a method for forming an antimicrobial insert within the interior of a medical device via an injection molding process. The method utilizes a medical device having an injection port formed in a sidewall of the medical device, wherein the injection port is in fluid communication with a non-tapered, interior surface of the device. The antimicrobial material is injected into the medical device after inserting a tapered mandrel into the interior of the medical device, wherein the antimicrobial material is injected into a wedge-shaped gap formed between the outer surface of the mandrel and the non-tapered, interior surface of the device.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 1A and 1B illustrate perspective views of inserts having tube shapes in accordance with representative embodiments of the present invention. FIG. 1C illustrates a top view of an insert having a tube shape with an irregular internal surface in accordance with a representative embodiment of the present invention. FIG. 1D illustrates a cross-sectional view of a tube-shaped insert that includes an expanded opening on one end in accordance with a representative embodiment of the present invention. FIGS. 1E and 1F illustrate inserts that include a reinforcing substructure in accordance with representative embodiments of the present invention. FIGS. 1G and 1H illustrate inserts that have a rod shape in accordance with representative embodiments of the present invention.

FIGS. 2A-2C illustrate a catheter adapter that includes one or more inserts in various positions in accordance with a representative embodiment of the present invention. FIG. 2D illustrates a ported intravenous catheter that includes inserts in accordance with a representative embodiment of the present invention. FIG. 2E illustrates a cap that includes a rod-shaped insert in accordance with a representative embodiment of the present invention.

FIG. 3A illustrates a prior art catheter adapter that employs a bump formed in the internal wall of the catheter adapter to hold the septum in place in accordance with a representative embodiment of the present invention. FIG. 3B illustrates how an insert can be used in place of a bump to retain the septum in accordance with a representative embodiment of the present invention.

FIG. 4A illustrates a peel-away sleeve prior to the sleeve being filled with a base material matrix in accordance with a representative embodiment of the present invention. FIG. 4B illustrates the peel-away sleeve after the sleeve has been filled with the base material matrix in accordance with a representative embodiment of the present invention. FIG. 4C illustrates the peel-away sleeve being peeled off of the insert after the base material matrix has been cured to form the insert in accordance with a representative embodiment of the present invention.

DETAILED DESCRIPTION OF THE INVENTION

Figure 1A:
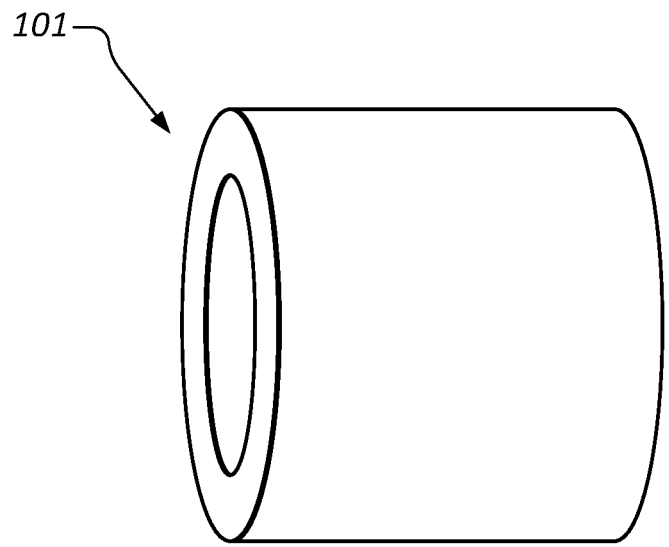
FIGS. 1A-1H each illustrate an insert in accordance with one or more embodiments of the invention.

The present invention extends to inserts for medical devices. The inserts are manufactured of a material that includes an antimicrobial agent and that has elution characteristics so that the antimicrobial agent is eluted from the material at a desired rate to provide antimicrobial protection to a medical device in which the insert is contained. An insert can be formed with a desired geometry to allow the insert to be compression fit within a medical device to prevent the insert from moving or becoming dislodged once inserted into the medical device. The material may also be hygroscopic so that the insert swells when subject to a fluid thereby enhancing the compression fit of the device within the medical device. In some cases, the material can be reinforced using an internal structure and/or an adhesive.

The inserts of the present invention can be used within a variety of medical devices to provide a desired level of antimicrobial protection to the medical devices. An insert can be designed to have a surface area that is sufficient for the volume of the location in which the insert is contained so that a sufficient amount of antimicrobial agent is eluted to disinfect the fluid within the area within a desired amount of time. Examples of medical devices or components in which the inserts of the present invention can be used include ports, stop cocks, male luers, female luers, IV sets, needleless connectors, respirators, catheters, devices for fluid infusion to the body or aspiration from the body, surgical instruments etc.

The inserts of the present invention can be manufactured in various ways. For example, the inserts can be formed in a desired geometry by casting, thermoforming, or extrusion. In some cases, the inserts can be formed using a peel-away sleeve. The peel-away sleeves can be formed of a non-sticky material which facilitates removal of the inserts once the inserts have cured.

In one embodiment, the present invention is implemented as an inset for a medical device. The insert comprises a base material having elution characteristics, and an antimicrobial agent contained within the base material so that the antimicrobial agent is eluted from the base material when the base material is exposed to or comes in contact with a fluid.

In some embodiments, the base material comprises a hygroscopic material that swells upon absorbing a fluid.

In some embodiments, the insert is bonded to a surface of the medical device using a curable adhesive.

In some embodiments, the insert is mechanically fastened to the medical device using features such as threads, snap-fits etc.

In some embodiments, the insert is made of a hydrophilic material to facilitate elution of a water soluble antimicrobial agent where the base material comprises a hydrophilic polymer such as urethane acrylate or a polyurethane polymer.

In some embodiments, the antimicrobial agent comprises between 0.1% and 40% w/w of the insert.

In some embodiments, the insert is formed by curing the base material containing the antimicrobial agent in a desired form. In some embodiments, the form comprises a tube shape or a rod shape. In some embodiments, the tube shape has an outer diameter that is equal to or larger than an inner diameter of a lumen of a medical device within which the insert will be placed.

In some embodiments, the insert is placed within a catheter adapter having a septum, wherein the insert secures the septum in place.

In some embodiments, the insert is formed within a peel-away sleeve. In some embodiments, the peel-away sleeve comprises one of: polyolefin; fluoropolymer; polyvinyl chloride; or ethylene vinyl acetate. In some embodiments, the insert is formed within a mold that is lined with one or more peel-away sheets.

In some embodiments, the insert comprises a reinforcing substructure contained within the base material.

In another embodiment, the present invention is implemented as a medical device comprising an insert that elutes an antimicrobial agent. The insert comprises a base material having elution characteristics, and an antimicrobial agent contained within the base material so that the antimicrobial agent is eluted from the base material when the base material is exposed to a fluid.

In some embodiments, the insert comprises a lumen through which fluid passes within the medical device.

In some embodiments, the insert attaches to and extends from a first medical device such that the insert is configured to contact and/or be inserted within a second medical device when the two medical devices are connected. As such, the eluted antimicrobial agent from the insert provides antimicrobial protection to both of the medical devices.

In another embodiment, the present invention is implemented as a method for forming an insert for a medical device. A base material having elution characteristics is combined with an antimicrobial agent to form a base material matrix. The base material matrix is then formed into an insert that is sized and shaped to be inserted and contained within a medical device.

In some embodiments, the base material matrix is formed into the insert using UV curing, heat curing, or heat forming.

In some embodiments, the insert contains materials that at least partially dissolve into the fluid resulting in partial or even complete dissolution of the insert upon use In some embodiments, they insert comprises a matrix, such as a cross-linked polymer or a ceramic, that does not dissolve in to the fluid while the antimicrobial agent contained within the matrix at least partially dissolves.

In some embodiments, forming the base material matrix into the insert comprises placing the base material matrix within a peel-away material.

In some embodiments, the method includes placing the insert within the medical device such that the insert is exposed to a fluid to cause the antimicrobial agent to elute from the insert into the fluid.

In some embodiments, the insert may serve a mechanical function such as a support feature for other components of the medical device or a fluid conduit or a mating feature to another device or component.

Antimicrobial inserts in accordance with one or more embodiments of the invention can be comprised of a base material matrix and one or more antimicrobial agents. In some embodiments, the base material matrix can be a UV curable, hydrophilic material that contains an antimicrobial agent with controlled release (elution) characteristics. Alternatively, a base material can be coated with an antimicrobial coating from which an antimicrobial agent will elute when subject to a fluid. Examples of materials that could be used to form the antimicrobial inserts of the present invention includes those disclosed in U.S. Pat. No. 8,512,294 titled Vascular Access Device Antimicrobial Materials And Solutions; U.S. patent application Ser. No. 12/397,760 titled Antimicrobial Compositions; U.S. patent application Ser. No. 12/476,997 titled Antimicrobial Coating Compositions; U.S. patent application Ser. No. 12/490,235 titled Systems And Methods For Applying An Antimicrobial Coating To A Medical Device; and U.S. patent application Ser. No. 12/831,880 titled Antimicrobial Coating For Dermally Invasive Devices. Each of these patent documents is incorporated herein by reference.

In one particular embodiment, the antimicrobial agent used to form an insert can be chlorhexidine including chlorhexidine diacetate (CHA) and chlorhexidine gluconate (CHG). However, any other antimicrobial agent that will elute from a base material or from a coating on a base material could be used.

Inserts may be formed using any suitable technique including in-mold curing, UV cured profile extrusion, cutting, sheet stamping, etc. A primary benefit of employing inserts to provide antimicrobial protection within medical devices is that the inserts can be formed in a separate process from the process used to form the medical devices. For example, unlike prior art approaches which apply an antimicrobial coating within the lumen of a catheter adapter or other medical device, the inserts of the present invention can be formed independently from the catheter adapter or other medical device and then inserted. In this way, the inserts can be manufactured much more easily and inexpensively when compared to prior art approaches.

Similarly, because the inserts are independent of the medical device in which the inserts will be used, antimicrobial protection can be more easily provided in a greater variety of devices. For example, some devices are made of a material that is not suited for antimicrobial coatings (e.g. an antimicrobial coating may not stick to the material). The inserts of the present invention, however, can be used within a medical device made of virtually any material to provide antimicrobial protection within the medical device.

In some embodiments, the base material used for an insert can be hygroscopic so that the base material will swell once contacted by a fluid, such as saline or blood. The swelling of the insert can increase the compression fit within the medical device to prevent the insert from moving or becoming dislodged during use. In this way, the use of inserts is further facilitated because no additional structure or securing mechanism (e.g. an adhesive or structural feature) may be required to retain the insert at the desired position within the medical device. As a result, medical devices can be provided with antimicrobial protection with greater ease and at a reduced cost. Of course, the inserts of the present invention could be used with a securing structure or mechanism if desired.

In some embodiments, the inserts can be partially cured prior to insertion in a medical device and then fully cured once within the medical device. In other embodiments, the inserts can be fully cured prior to being inserted.

In some embodiments, it may be desirable to increase the strength or rigidity of an insert. In such cases, the insert can include a reinforcing substructure that is contained within the base material. Examples of suitable reinforcing substructures include metals, plastics, fibers, etc. For example, when an insert is formed as a tube, a tube-shaped reinforcing structure can be contained within the base material.

The shape and size of an insert can be configured so that the rate of elution of the antimicrobial agent is sufficient to provide a desired level of antimicrobial protection. The rate of elution of the antimicrobial agent is dependent on the surface area of the insert that is exposed to the fluid. Accordingly, various shapes and sizes of inserts can be employed to obtain the necessary surface area to provide the desired amount of antimicrobial protection. In some embodiments, the ratio of the insert's exposed surface area to fluid volume (i.e. the volume of fluid to be treated by the antimicrobial agent within the insert) is between 0.1 $cm^2$/ml and 50 $cm^2$/ml.

In some embodiments, an insert may be contained within or separated from the fluid volume by a hydrophilic filter membrane. A hydrophilic filter membrane can be used to further control the elution characteristics of the base material (e.g. by controlling the flow of fluid along the surface area of the insert) and can also prevent any particles that break off from the insert from passing into the fluid stream. An example of a material suitable for use as a hydrophilic filter includes polyethersulfone (PES).

Any material having elution characteristics can be employed as the base material of an insert. Examples of suitable materials include UV cured acrylate-urethanes and heat-cured polymers which soften in water, such as hygroscopic polyurethanes. These materials can be preferred over materials that do not soften in water because they enhance the compression fit of the inserts when they are wet.

The amount of antimicrobial agent used within the matrix can be varied to provide a desired mechanical property or elution characteristic. For example, in some instances a matrix is provided which comprises solid antimicrobial agent particles in an amount representing approximately 0.1-40% w/w of the matrix. These particles may range in size from 100 nm (fine powder) to 0.15 mm (salt-sized crystals). Additional additives may also be used to attain a particular characteristic. These additional additives include: multiple antimicrobial agents to widen the spectrum of microbes that will be affected; viscosity modifiers such as silica; color modifiers such as dyes or titanium dioxide; strength or stiffness modifiers such as glass fibers, ceramic particles such as zirconia, or metallic fibers; radiopacity modifiers such as barium sulfate; and magnetic susceptibility enhancers such as gadolinium chelates.

Inserts in accordance with the present invention can be formed in various shapes and sizes and can be used in various types of medical devices and for various functions. Examples of the different types of inserts that are encompassed within the present invention are provided in the figures and will be described below.

Figure 1B:
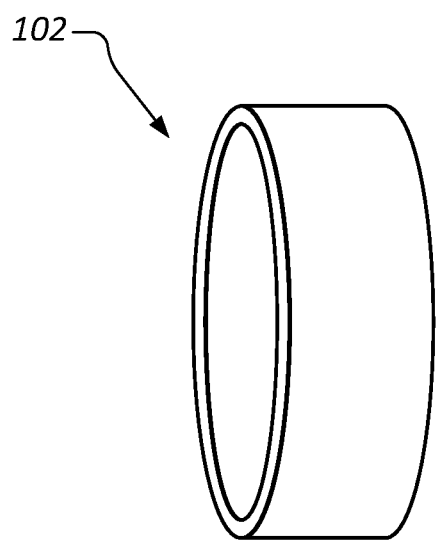

Referring to FIGS. 1A-1H, antimicrobial inserts according to embodiments of the invention can be formed in various shapes and sizes as necessary for use in a particular medical device. For example, FIGS. 1A and 1B illustrate examples of tube-shaped inserts 101 and 102 respectively. Inserts 101 and 102 can be formed to have an outer diameter that is approximately the same as or slightly larger than the inside diameter of a lumen of a medical device. In this way, inserts 101 and 102 can be compression fit within the lumen of the medical device to impart antimicrobial protection within the lumen.

In some embodiments, inserts 101 and 102 can be designed only to form a channel through which a fluid within the lumen of the medical device flows. As the fluid contacts and flows through inserts 101 and 102, an antimicrobial agent contained within the material of the inserts 101 and 102 is eluted into the fluid thereby killing any microbes that may be present within the fluid. In such cases, the inner diameter of inserts 101 and 102 can be configured so as to not significantly restrict fluid flow through the lumen or to provide a desired flow characteristic through the lumen.

In other embodiments, the inner diameters of inserts 101 and 102 are configured to conform to the outer diameter of another device which is inserted into the lumens of inserts 101 and 102. In such cases, inserts 101 and 102 are placed so that the inserted device contacts the antimicrobial agent contained within the material of inserts 101 and 102 thereby killing any microbes which may be present on the outer surfaces of the inserted device.

Figure 1C:
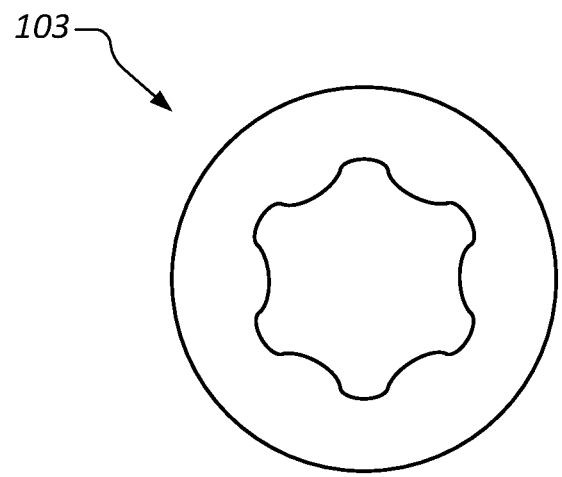

In some embodiments, the inner surface of a tube-shaped insert can have a varying or irregular diameter to increase the surface area that is exposed to a fluid. FIG. 1C illustrates an example of a tube-shaped insert 103 that has an inner surface with a varying diameter. The ridges and channels formed within the inner surface effectively increase the surface area of insert 103 that is exposed to a fluid.

In addition to tube-shaped inserts that have a generally circular opening, inserts having other external and internal shapes can be formed. For example, some inserts can have an internal opening or lumen that is in the shape of a plus sign, a star, a square, etc. Also, some inserts can have an outer surface that has a triangular, square, or rectangular cross-section. Accordingly, inserts can be formed in any desired shape and/or size to fit within an intended medical device.

Figure 1D:
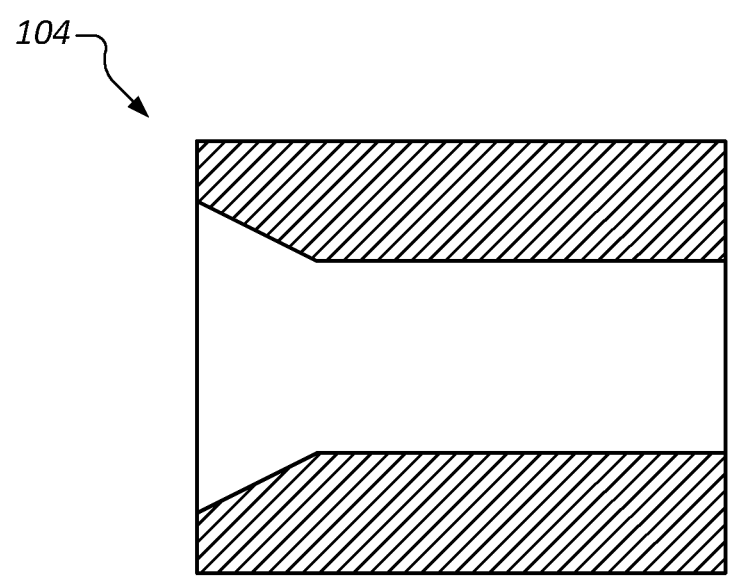

FIG. 1D illustrates an example of an insert 104 having an expanded opening on one end. The expanded opening can facilitate use of insert 104 with another device. For example, insert 104 could be placed within the lumen of a port or a female luer so that, when another device (e.g. a male luer) is inserted into the port or female luer, the other device may insert into the expanded opening.

Figure 1E:
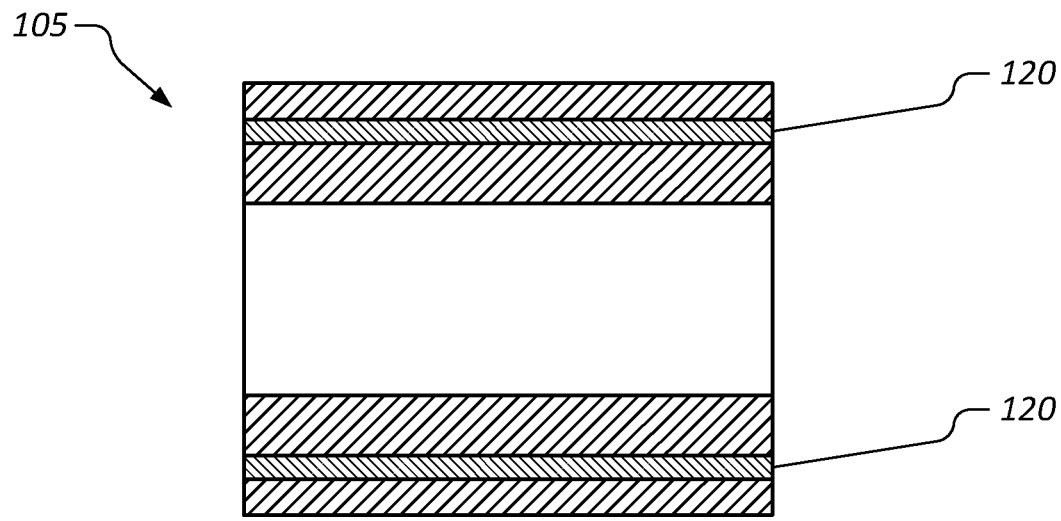
Figure 1F:
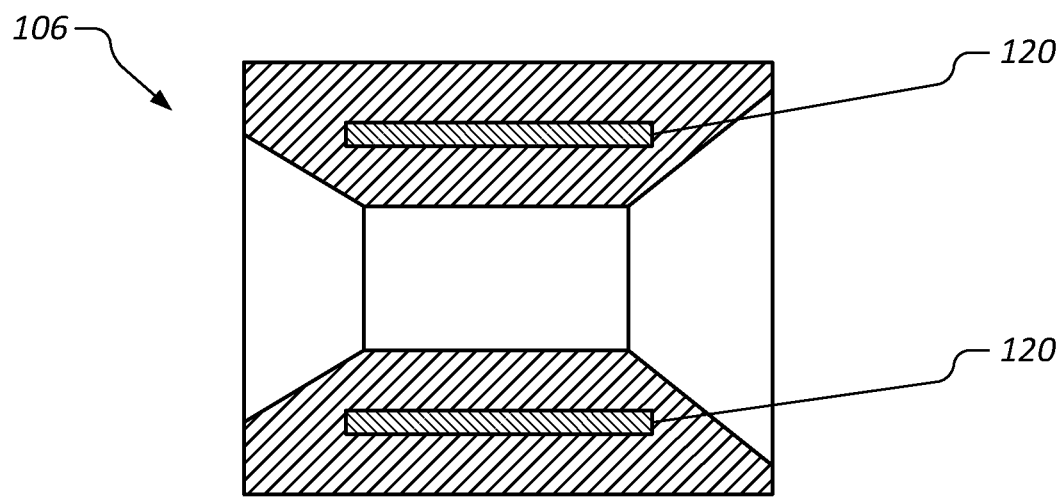

FIGS. 1E and 1F illustrate examples of inserts 105 and 106 that include a reinforcing substructure 120. The reinforcing substructure 120 can extend the full length of the insert as is shown in FIG. 1E or only along a portion of the length as is shown in FIG. 1F. In the examples shown in FIGS. 1E and 1F, the reinforcing substructure 120 comprises a tube shape to conform to the tube shape of inserts 105 and 106. However, a reinforcing substructure can have other shapes that do not conform to the shape of the insert as long as the reinforcing substructure can be contained within the material of the insert. Also, in some embodiments, more than one reinforcing substructure can be employed within an insert. For example, two or more rings of reinforcing substructure could be employed within a tube-shaped insert. In some embodiments, the reinforcing substructure can be comprised of fibers that are mixed with the base material to form a reinforced composite base material.

With reference again to inserts 105 and 106, reinforcing material 120 can serve to enhance the compression fit of inserts 105 and 106 within the lumen of a medical device. For example, reinforcing material 120, which is in the shape of a tube, can have an outer diameter that is slightly less than the inside diameter of the lumen in which the insert will be placed. Accordingly, once the inserts are inserted into the lumen, the inside wall of the lumen and the outside surface of the reinforcing material will compress the base material of the inserts to securely hold the inserts in place.

Figure 1G:
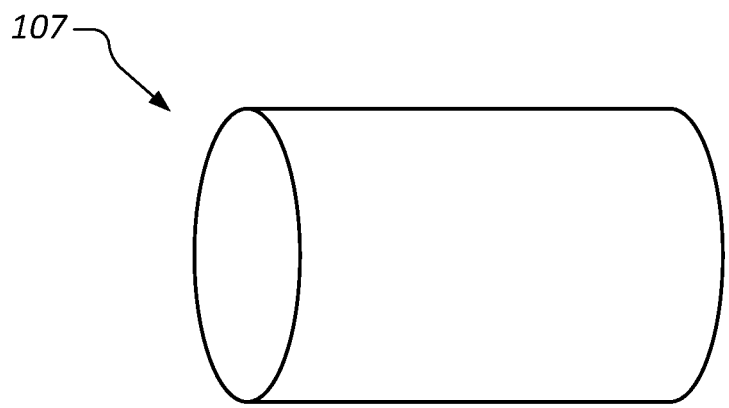
Figure 1H:

FIGS. 1G and 1H illustrate additional examples of inserts 107 and 108. In contrast to inserts 101-106, inserts 107 and 108 are formed in a rod shape. Such rod-shaped inserts can be used in various ways including within a cap or device that is inserted into the lumen of another device. As described above, reinforcing material can be used to increase the rigidity of inserts 107 and 108 and to prevent inserts 107 and 108 from breaking. Although not shown, rod-shaped inserts can be formed that have non-circular cross-sections. For example, the cross-sectional shape of a rod can be star-shaped to increase the surface area of the insert.

Figure 2A:
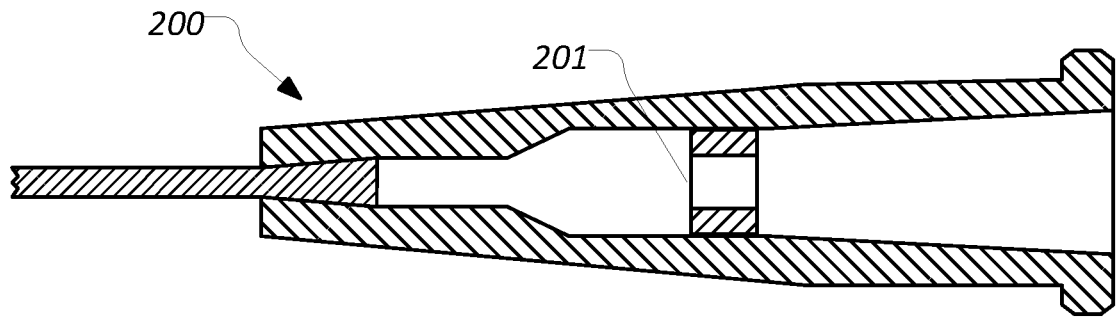
FIGS. 2A-2E illustrate examples of medical devices in which inserts configured in accordance with one or more embodiments of the invention can be placed.
Figure 2B:
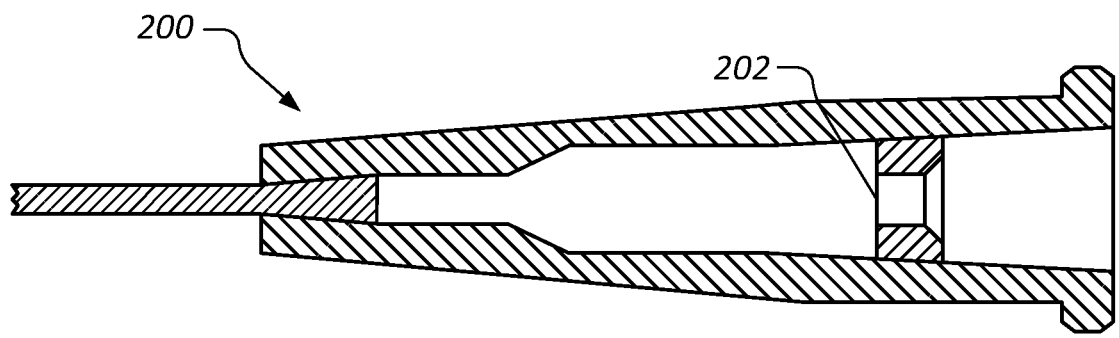
Figure 2C:
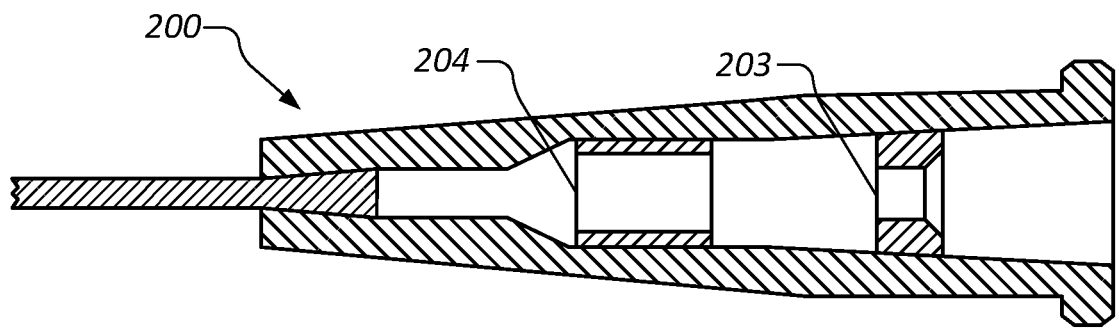

FIGS. 2A-2E illustrate examples of various devices in which inserts can be used to provide antimicrobial protection within the devices. FIGS. 2A-2C illustrate various locations within a catheter adapter 200 where an insert may be placed. In FIGS. 2A and 2B, a single insert 201 and 202 respectively is placed within the lumen of catheter adapter 200. In FIG. 2C, two inserts 203 and 204 are placed within the lumen of catheter adapter 200. As shown, inserts 201-204 have different shapes and sizes depending on the intended purpose of the insert.

Figure 2D:
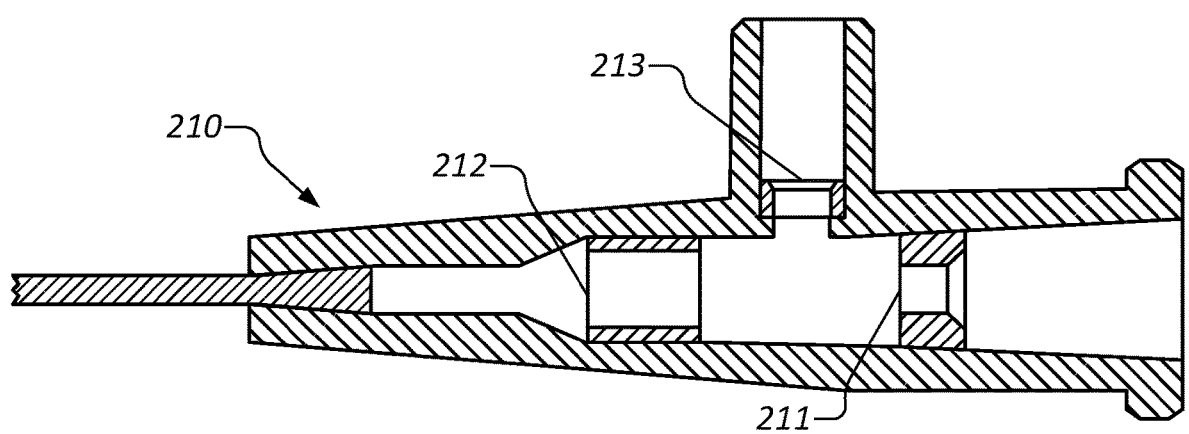

FIG. 2D illustrates an example where a ported intravenous catheter (PIVC) 210 includes three inserts 211, 212, and 213. The size and shape of each insert 211, 212, and 213 can be designed to impart the desired antimicrobial protection to the location of the insert. For example, insert 213 can be configured with a surface area and/or an elution rate so that an adequate amount of antimicrobial agent is eluted into fluid being injected through the port of the PIVC.

In each of the embodiments shown in FIGS. 2A-2D, the inserts can be manufactured independently of the catheter adapters and then inserted into the catheter adapters after manufacturing. Because inserts can be manufactured at minimal cost and can be easily added to the catheter adapter by insertion, there is little additional cost for producing catheter adapters that provide antimicrobial protection. This is in contrast to the substantial additional cost required to add an antimicrobial coating or lubricant on the inner surfaces of catheter adapters as is the case with prior art approaches.

Figure 2E:
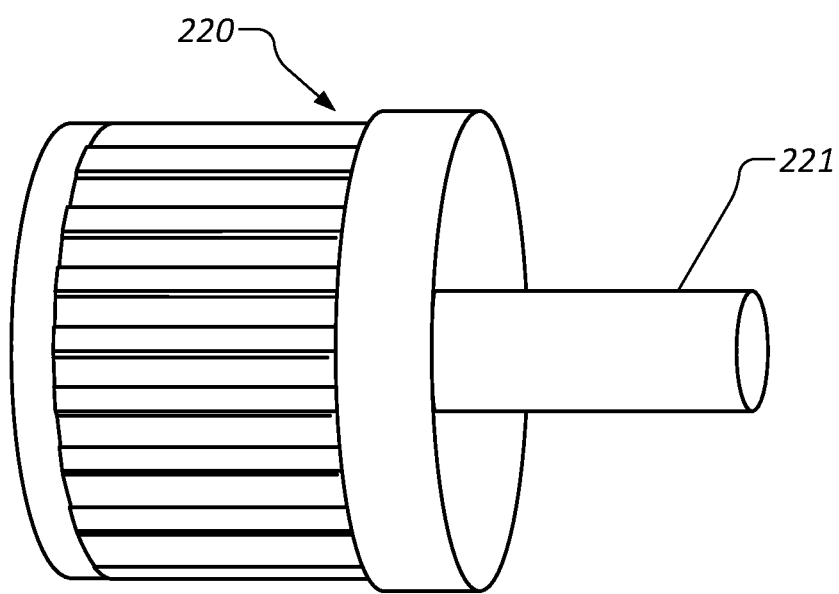

FIG. 2E illustrates an example where a cap 220 includes a rod-shaped insert 221. Cap 220 may be configured to attach to a port, female luer, or other opening of a medical device. In such cases, insert 221 can be configured to insert into the port, female luer, or other opening where the insert will be exposed to fluid. The elution of an antimicrobial agent from insert 221 can provide antimicrobial protection to the port, female luer, or other opening of the device. Because insert 221 can be manufactured independently of cap 220, caps which provide antimicrobial protection can be manufactured more easily and cheaply than with current techniques.

Figure 3A:
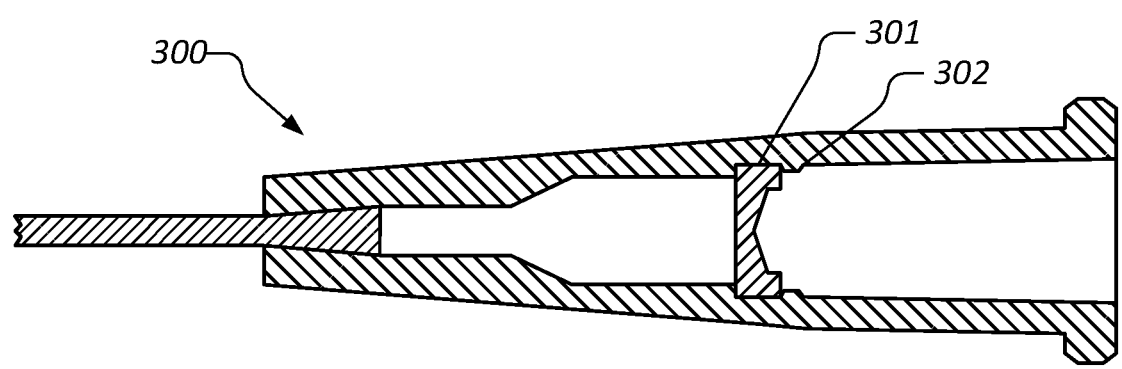
FIGS. 3A and 3B illustrate how an insert can be used to retain a septum in place within a catheter adapter in accordance with a representative embodiment of the present invention.
Figure 3B:
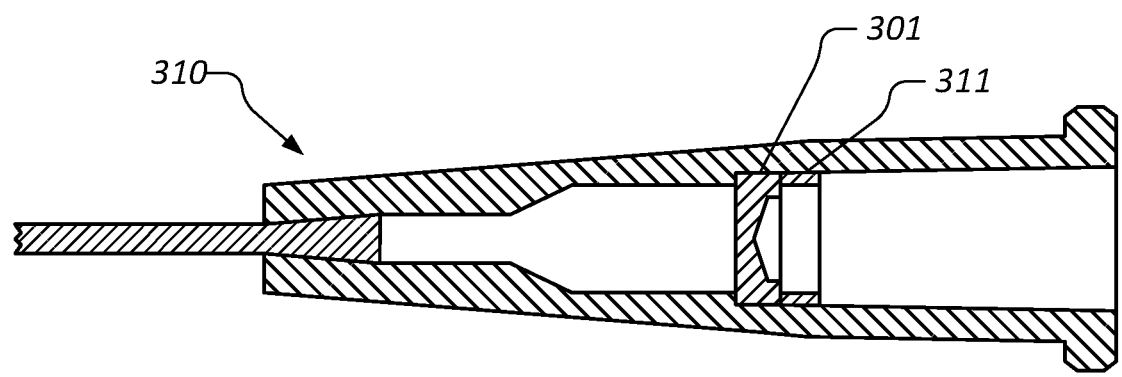

In some embodiments, the inserts of the present invention can perform functions in addition to providing antimicrobial protection. FIGS. 3A and 3B illustrate one example of how an insert can perform additional functions. FIG. 3A illustrates a common prior art catheter adapter 300 that employs a septum 301 for controlling the flow of blood within the catheter adapter. Septum 301 is designed to form a seal around an introducer needle that passes through the septum and to remain sealed when the introducer needle is removed from the catheter adapter and until another device is inserted through the septum.

To ensure that septum 301 remains in place while the introducer needle is withdrawn and when other devices are inserted through the septum, the inner surface of catheter adapter 300 includes a bump 302. Although bump 302 is effective in retaining septum 301 in place, the use of bump 302 can increase the cost of manufacturing catheter adapter 300 or may make it difficult to apply an antimicrobial coating within catheter adapter 300.

As shown in FIG. 3B, bump 302 can be replaced by an insert 311 which holds septum 301 in place. In other words, by placing insert 311 adjacent to septum 301, insert 311 can hold septum 301 in place. As a result, catheter adapter 310 can be designed without bump 302. Additionally, as described above, insert 311 can provide antimicrobial protection within the lumen of catheter adapter 310.

As described above, insert 311 can be configured to form a tight compression fit within catheter adapter 310. This compression fit can be enhanced in some embodiments by employing a hygroscopic base material so that insert 311 will swell when subject to a fluid. Similarly, one or more reinforcing substructures can be employed as desired to give insert 311 the necessary strength or structural rigidity to hold septum 301 in place.

Alternatively, insert 311 can be comprised of a material that may not include elution characteristics (i.e. that does not elute an antimicrobial agent). In such cases, an antimicrobial coating can be applied to insert 311 to provide the desired antimicrobial protection within the lumen of catheter adapter 310. In such embodiments, insert 311 can provide the benefit of allowing a material suitable for a particular antimicrobial coating to be used to hold septum 301 in place. Examples of suitable materials include polycarbonate and co-polyester. In contrast, in prior art catheter adapter designs, the material (of which bump 302 was made) typically was not ideal for the application of an antimicrobial coating. By employing insert 311, catheter adapter 310 can be made of any desired material (whether or not the material is suitable for the application of an antimicrobial coating) because the antimicrobial protection is provided by insert 311.

Whether insert 311 is comprised of a material that elutes an antimicrobial agent or that is coated with an antimicrobial agent, the insert provides both functions of securing septum 301 in place and disinfecting the lumen of catheter adapter 310. In this way, the manufacture of catheter adapters that include antimicrobial protection can be facilitated.

The inserts of the present invention can be made in many different ways including by pouring or injecting an unpolymerized formulation into an open mold for UV curing or into an injection mold for heat curing. Also, some inserts can be formed using extrusion or coextrusion over a substrate material. Similarly, some inserts can be formed using thermoplastics such as polyurethane which may be shaped using heat stamping.

Figure 4A:
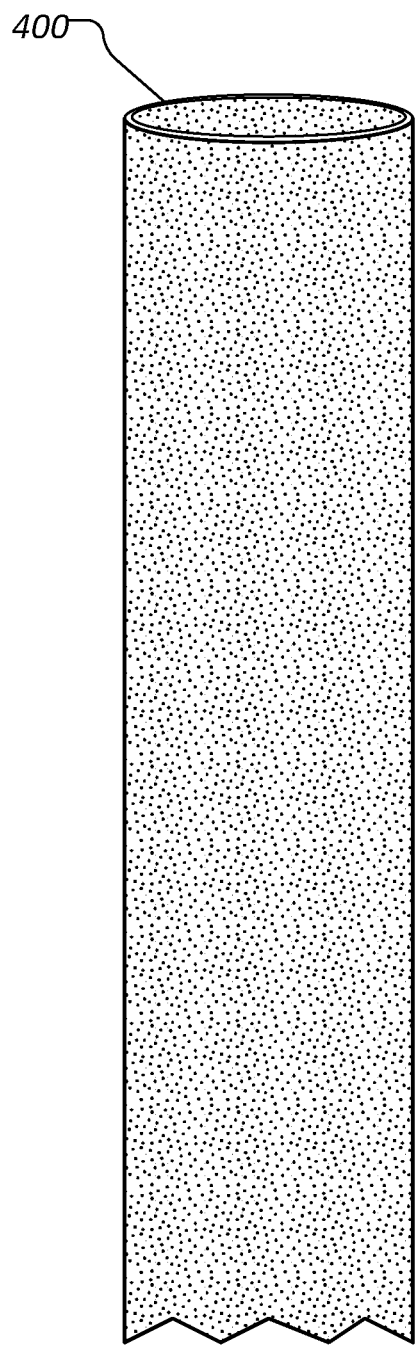
FIGS. 4A-4C illustrate how an insert can be formed using a peel-away sleeve in accordance with various representative embodiments of the present invention.
Figure 4B:
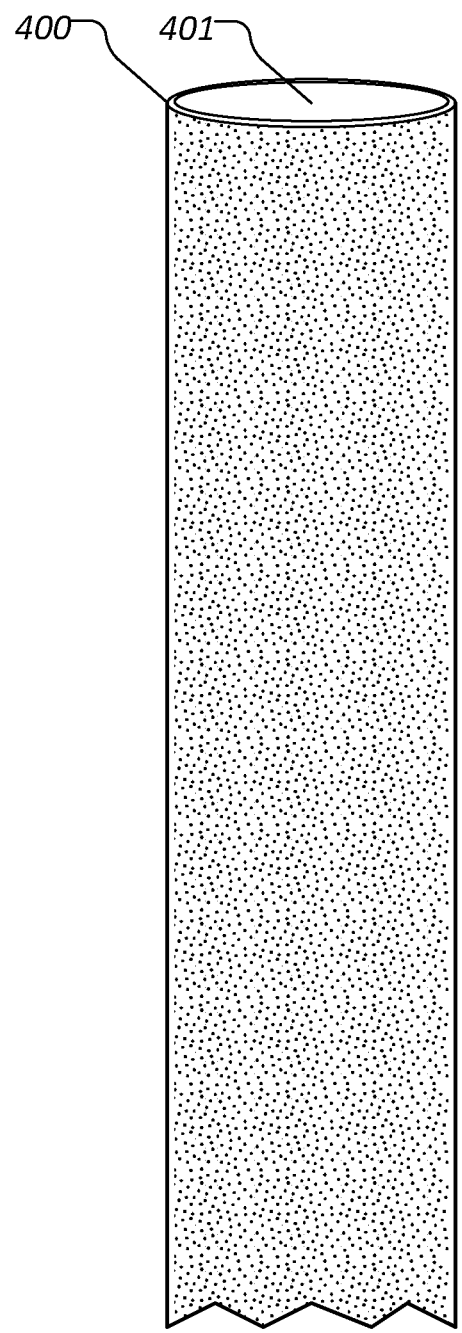
Figure 4C:
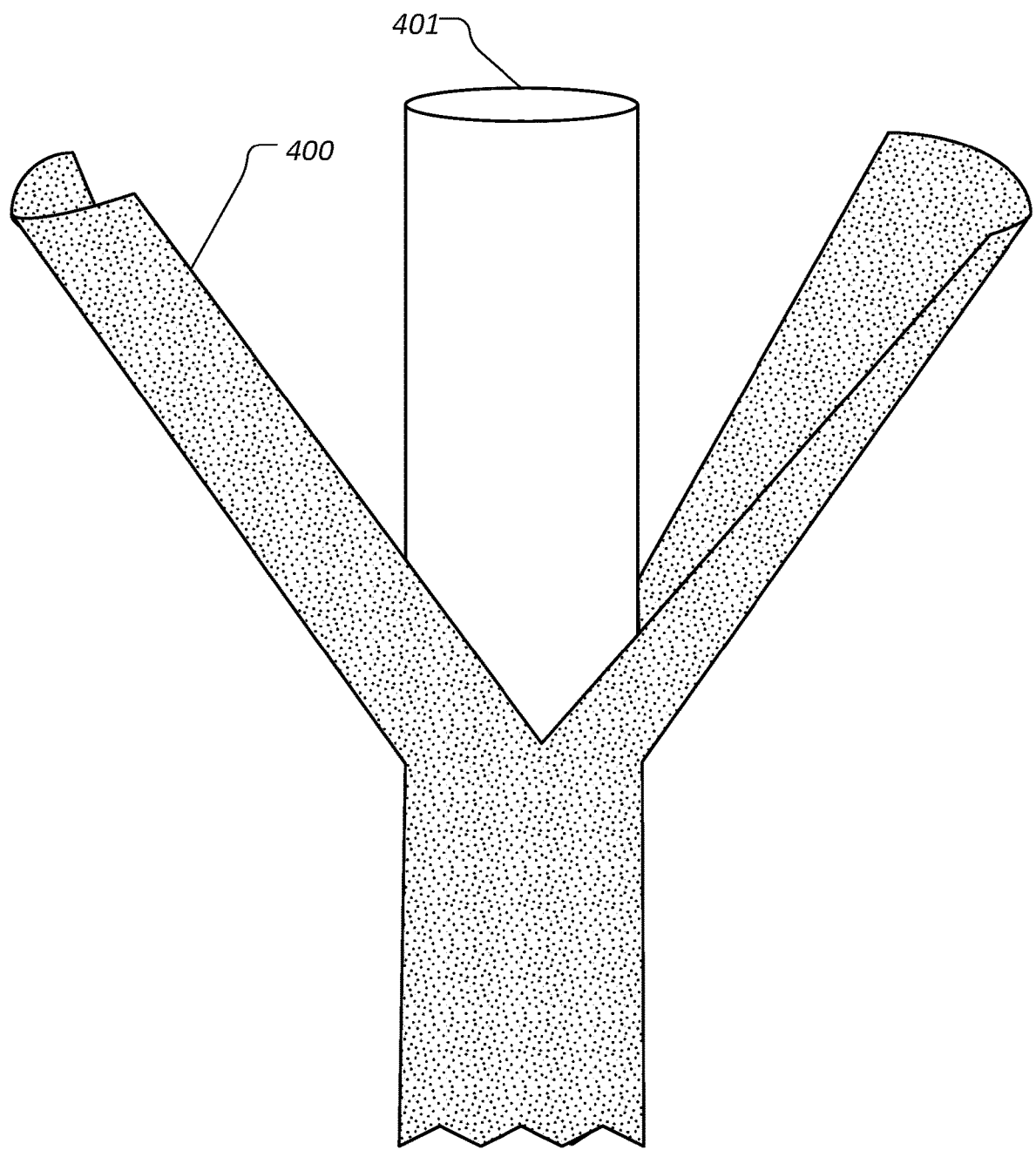

One particular example of how inserts can be formed is shown in FIGS. 4A-4C. These figures illustrate the use of a peel-away sleeve as a mold for forming inserts having a rod shape. FIG. 4A illustrates a peel-away sleeve 400 prior to being filled with an uncured base matrix. Peel-away sleeve 400 can be made of a material that has a low peel strength so that, once the matrix has been cured, the sleeve can be easily peeled away. The low peel strength of the sleeves ensures that the inserts will have a smooth exterior surface. The use of sleeves also minimizes the occurrence of flash on the inserts.

For example, for inserts that are made of an acrylate-based or a cyanoacrylate-based material, the sleeve can be made of polyolefin, fluoropolymer, polyvinyl chloride, or ethylene vinyl acetate. Examples of suitable polyolefin include polyethylene (low density, liner low density, high density, ultra-high molecular weight polyethylene, and derivatives thereof) and polypropylene (polypropylene homopolymer, polypropylene copolymer, and derivatives thereof). Examples of suitable fluoropolymer include polytetrafluoroethylene, fluorinated ethylene-propylene, polyvinylidene fluoride, polyethylenetetrafluoroethylene, and derivatives thereof.

Sleeve 400 can be formed in any suitable manner including by extrusion, molding, of thermoforming. Once formed, sleeve 400 can be filled with the base matrix 401 (e.g. CHA or CHG mixed in acrylate adhesive) as is shown in FIG. 4B. The base matrix is then cured using, for example, UV light, LED light, heat, etc. The sleeve 400 is then easily peeled away from the cured matrix 401 as shown in FIG. 4C leaving the insert material which may be cut to size as necessary.

Figure 5A:
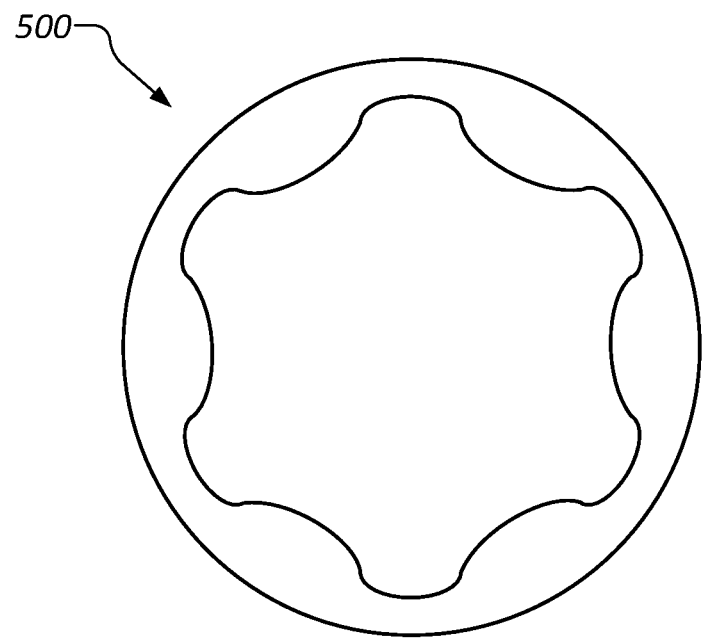
FIG. 5A illustrates a top view of a peel-away sleeve having an irregular internal surface in accordance with a representative embodiment of the present invention.
Figure 5B:
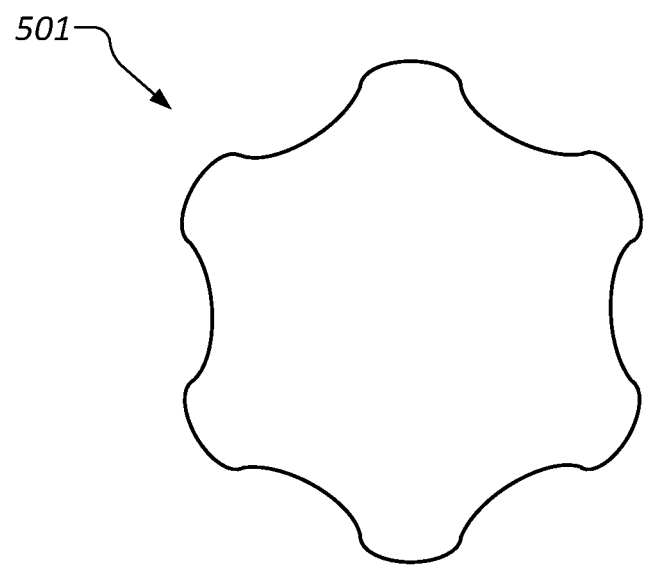
FIG. 5B illustrates a top view of an insert that can be formed using the peel-away sleeve of FIG. 5A in accordance with a representative embodiment of the present invention.

Sleeves of various shapes and sizes can be used to form a tube of a desired shape or size. For example, FIG. 5A illustrates a sleeve 500 with a varied internal diameter that can be used to form an insert 501 having a cross-sectional shape of increased surface area.

Figure 5C:
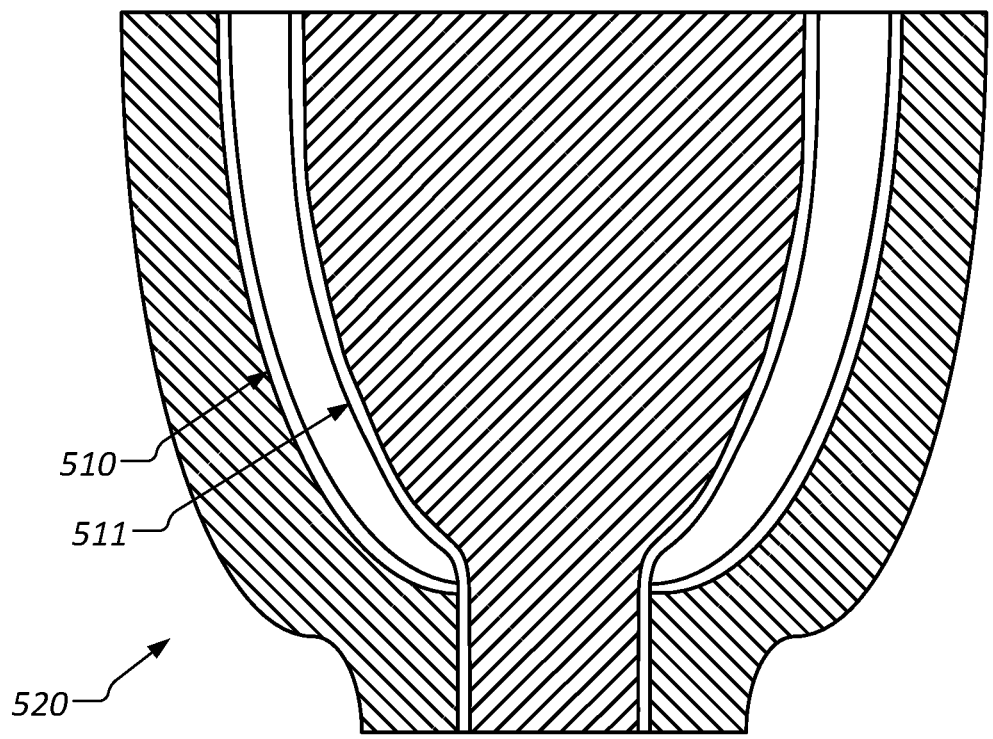
FIG. 5C illustrates a cross-sectional view of a mold that is lined with a peel-away material in accordance with a representative embodiment of the present invention.
Figure 5D:
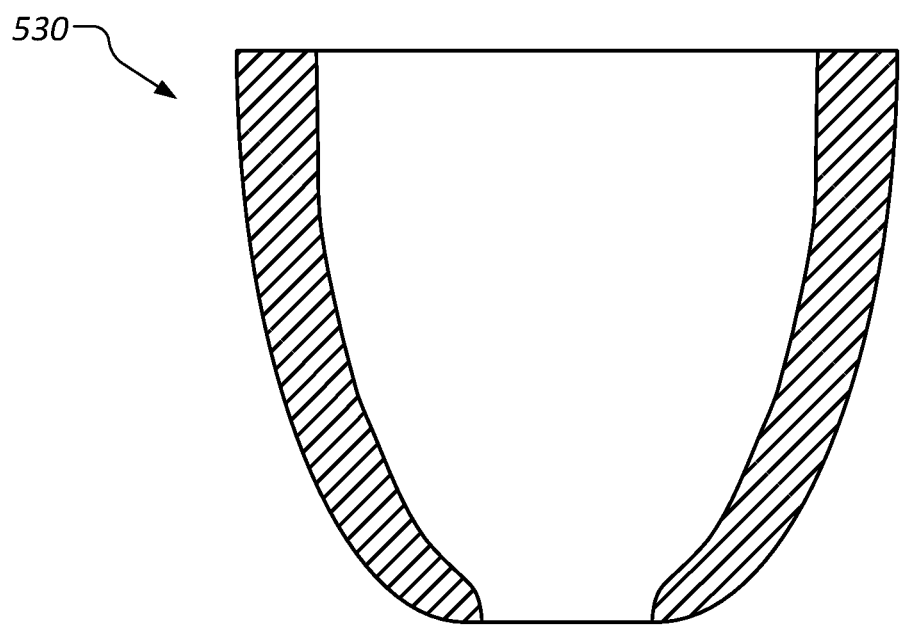
FIG. 5D illustrates a cross-sectional view of an insert that can be formed using the mold of FIG. 5C in accordance with a representative embodiment of the present invention.

In some embodiments, rather than filling the sleeve with the base matrix (i.e. rather than using the sleeve as the mold), a sheet made of a similar material as sleeve 400 can be used as a liner of a cast or molding tool. For example, FIGS. 5C and 5D illustrate a cross-sectional view of peel-away sheets 510 and 511 that are used as liners for a mold 520. A base matrix can be poured into mold 520 between sheets 510 and 511 and then cured. Once cured, the cured matrix contained within the sheets 510 and 511 can be removed from mold 520. Sheets 510 and 511 can then be easily peeled from the cured matrix leaving an insert 530 as shown in FIG. 5D. Insert 530 is an example of an insert that can be placed within a port to provide antimicrobial protection to fluid contained within the port. Similarly techniques can be employed to form a tube-shaped insert such as those shown in FIGS. 1A-1F or inserts of other shapes.

Figure 6:
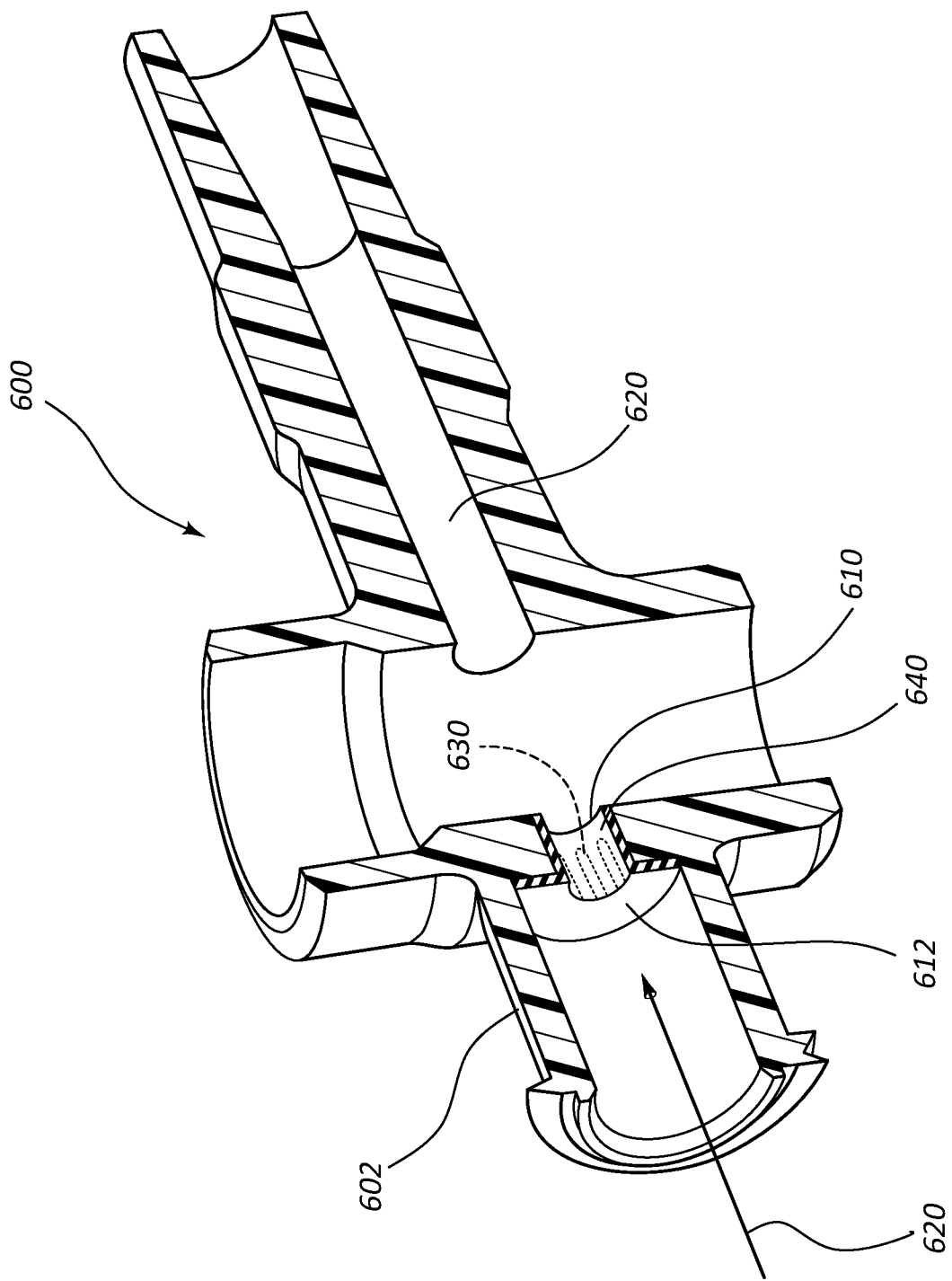
FIG. 6 illustrates a cross-sectional view of a stopcock medical connector having a female luer fitting in which is seated an antimicrobial luer stopper in accordance with a representative embodiment of the present invention.

Referring now to FIG. 6, some embodiments of the present invention further include an antimicrobial insert comprising a luer stopper 610 that is fitted within a female luer fitting 602 of a medical device 600, such as a stopcock or medical connector. Luer stopper 610 are generally configured or designed to contact the front or distal end of a male luer device upon insertion into a female luer fitting 602. Luer stopper 610 may prevent over-insertion of a male luer device. Luer stopper 610 may further provide correct alignment of the male luer device within fitting 602.

Figure 7A:
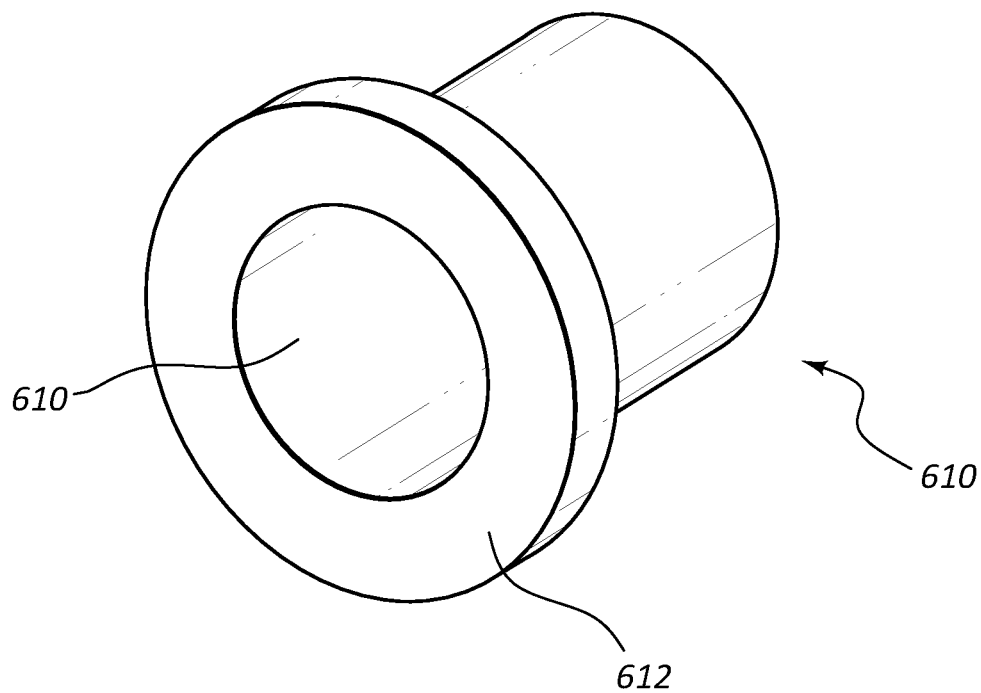
FIG. 7A illustrates a perspective view of an antimicrobial luer stopper in accordance with representative embodiments of the present invention.

In some instances, luer stopper 610 comprises a polymer material having antimicrobial properties. In some instances, luer stopper 610 comprises an antimicrobial coating material that is applied to the outer surface of luer stopper 610. For example, in some embodiments an antimicrobial coating is applied to the flange surface 612, shown in FIGS. 6 and 7A. In some embodiments, an antimicrobial coating is applied to one or more surfaces that are in direct contact with a fluid that is present within a fluid pathway 620 through medical device 600. Following an infusion procedure, any stagnant fluid remaining in luer fitting 602 is in fluid communication or contact with the antimicrobial luer stopper 610, or an antimicrobial coating applied thereon, whereby an antimicrobial agent within the stopper or coating material is eluted into the stagnant fluid to prevent the growth and/or colonization of microbes. In some instances, luer stopper 610 prevents the infusion of live microbes, as well as prevents the growth of biofilm within the device 600.

Figure 7B:
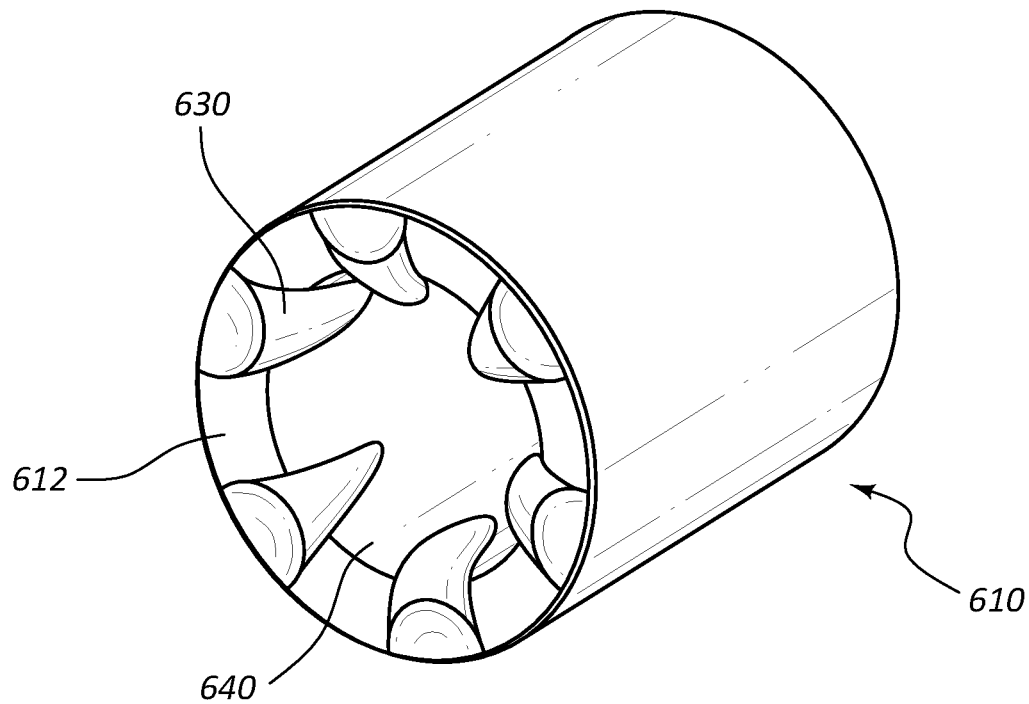
FIG. 7B illustrates a perspective view of the antimicrobial luer stopper in accordance with representative embodiments of the present invention.

Some embodiments of luer stopper 610 further comprise one or more tabs 630, as shown in FIGS. 6 and 7B. Tabs 630 are generally provided to assist in accurately positioning a luer connector within female luer fitting 602. In some instances, tabs 630 are provided to achieve a proper insertion depth of a luer connector, and to ease removal of the luer connector from fitting 602. In some instances, tabs 630 further comprise an antimicrobial coating material, wherein the thickness of the coating material does not interfere with the actuation or removal of the male luer connector.

The number and size of tabs 630, as well as the concentration of the antimicrobial agent within the antimicrobial coating may be varied to optimize microbial kill efficacy with regards to elution rate and duration. In some instances, tabs 630 are formed in a continuous ring or luer stopper having a top surface and or side surfaces that are coated for maximal microbial effects or kill duration. For example, in some embodiments to top or flange surface 612 comprises a surface area of 0.001 in$^2$. In other embodiments, luer stopper 610 comprises an interior surface area 640 from 0.012 in$^2$ to 0.02 in$^2$, wherein the luer stopper 610 is molded to extend into a port portion of the medical device 600, as shown. Further, in some embodiments luer stopper 610 comprises 2, 3, 4, 5, 6, or more tabs 630. The addition of tabs 630 may increase the surface area of luer stopper 610, thereby providing for additional surface area that may be coated with an antimicrobial coating. Thus, both the antimicrobial concentration and surface area can be optimized to achieve the targeted kill rate and duration.

The flange surface 612, tabs 630, and interior surface 640 may be coated with an antimicrobial coating according to any known method. In some embodiments, the aforementioned surfaces may be coated via a pad print method. In other embodiments, the aforementioned surfaces may be coated by simply dispensing antimicrobial coating drops onto the desired surfaces. The coating material is then cured using UV light, LED light, or heat. As many IV access components are transparent or translucent, a fast UV/LED light cure can be achieved for high productivity.

Figure 8A:
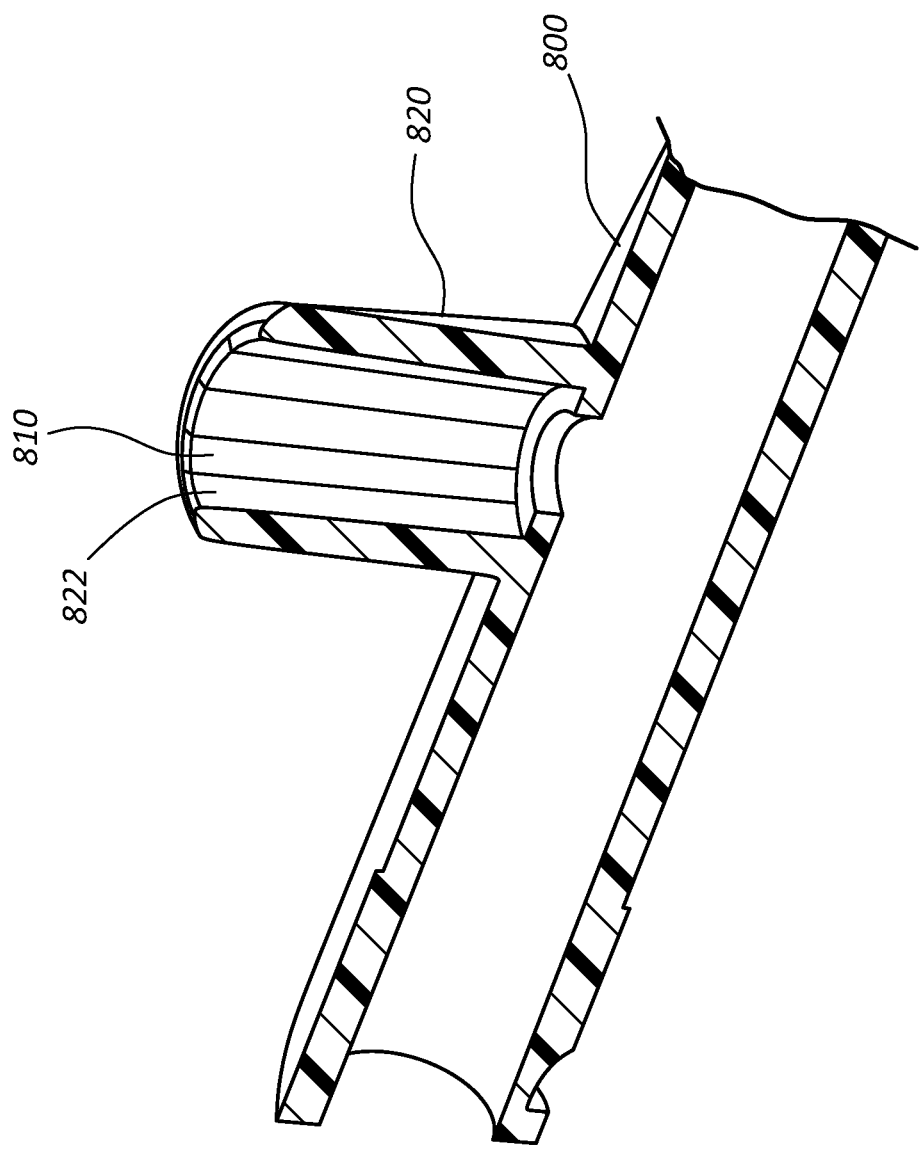
FIG. 8A illustrates a cross-sectional view of a catheter adapter having a side port with interior grooves comprising an antimicrobial material in accordance with a representative embodiment of the present invention.
Figure 8B:
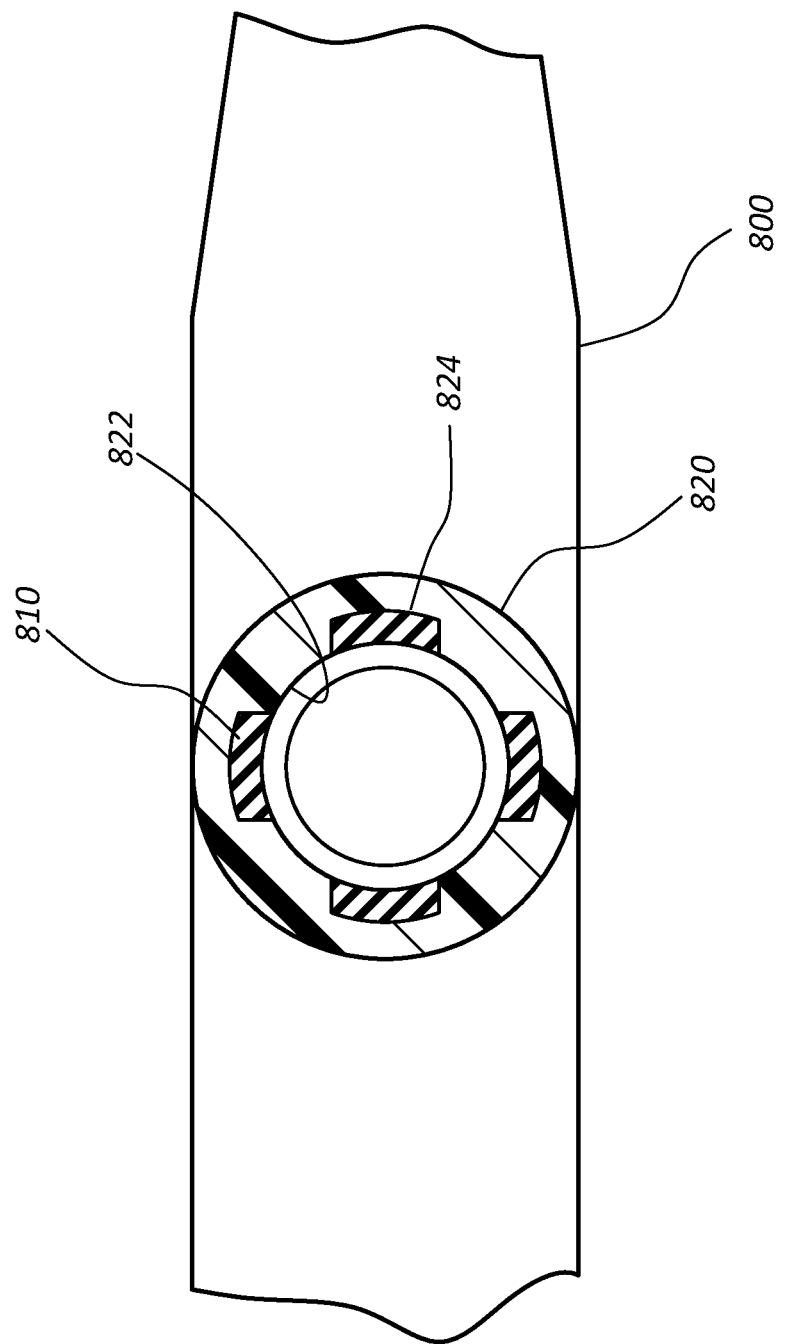
FIG. 8B illustrates a top plan view of the catheter adapter having the side port with interior grooves comprising the antimicrobial material in accordance with a representative embodiment of the present invention.

Referring now to FIGS. 8A and 8B, some embodiments of the present invention further include an antimicrobial insert comprising strips 810 that are applied to the inner surface 822 of a side port 802 of a medical device 800, such as a catheter adapter. Strips 810 may comprise an antimicrobial, polymer material having an antimicrobial agent that is configured to elute out of the polymer material when contacted by a fluid. In some embodiments, strips 810 are coated with an antimicrobial coating, wherein an antimicrobial agent within the antimicrobial coating is configured to elute out of the antimicrobial coating when exposed to or contacted by a fluid.

In some embodiments, inner surface 822 comprises recessed channels 824 having a width, depth, and length configured to receive strips 810. Strips 810 may be retained within channels 824 via any suitable method, for example, such as by an adhesive or plastic welding. In some embodiments, strips 810 are formed within channels 824 via an injection molding process whereby a mandrel is first fitted into side port 802 to provide a gap between the outer surface of the mandrel and channels 824. Antimicrobial material is then injected into channels 824. The inserted mandrel retains the injected antimicrobial material within channels 824 until the antimicrobial material is cured, such as by UV radiation. The mandrel is then removed from side port 802. In some instances, the outer surface of the mandrel is coating with non-stick or releasing material prior to insertion within side port 802, thereby preventing adhesion between strips 810 and the outer surface of the mandrel.

Figure 9:
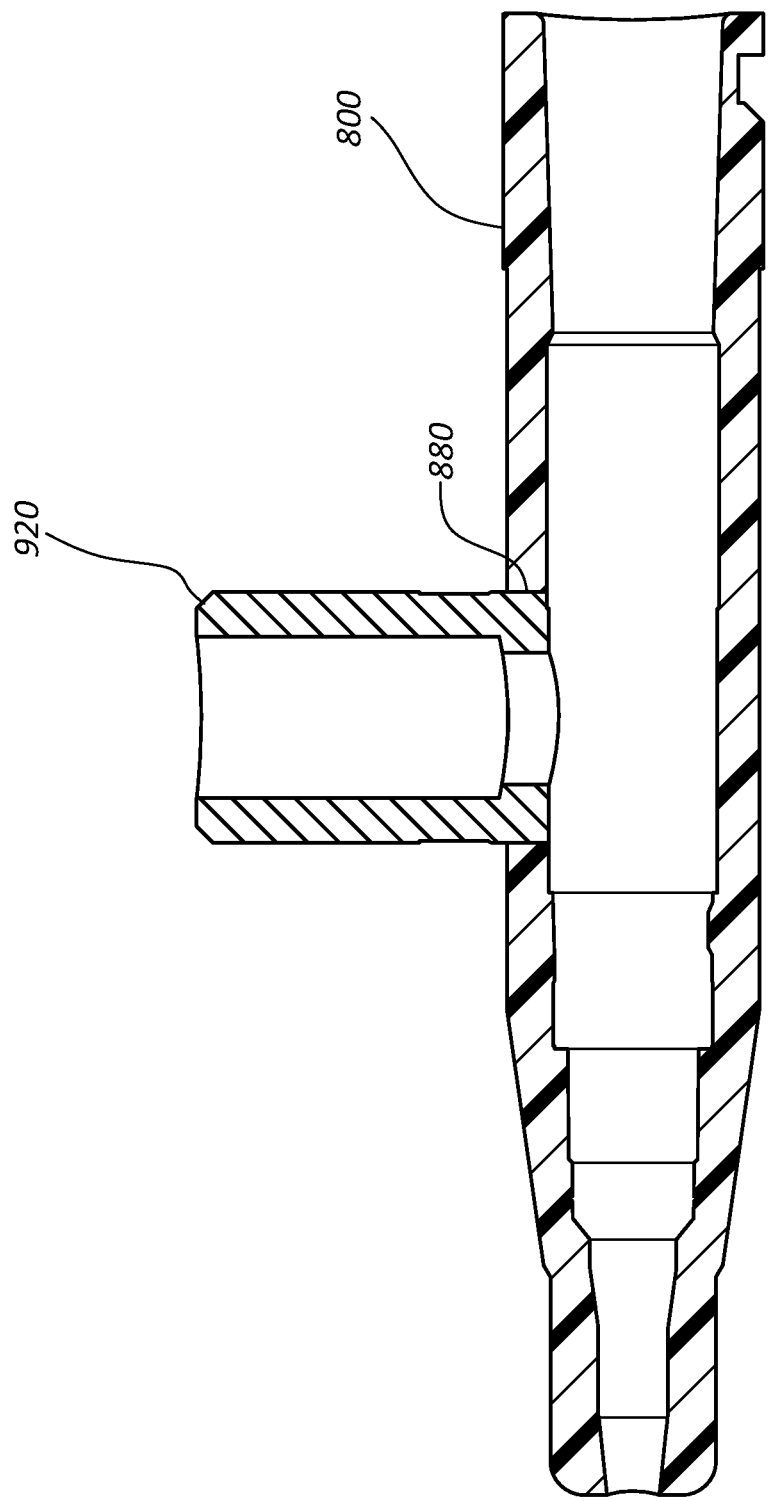
FIG. 9 illustrates a cross-sectional side view of a catheter adapter comprising an antimicrobial side port that has been welded into the catheter adapter in accordance with a representative embodiment of the present invention.

In some embodiments, medical device 800 comprises an antimicrobial side port 920, as shown in FIG. 9. Antimicrobial side port 920 generally includes a polymer material comprising an antimicrobial agent configured to elute out of the polymer material when exposed to a fluid. In some instances, medical device 800 comprises an opening 880 having a diameter that is configured to receive antimicrobial side port 920. Side port 920 is permanently secured within opening 880 via one or more known methods, for example, such as by an adhesive or plastic welding.

Figure 10:
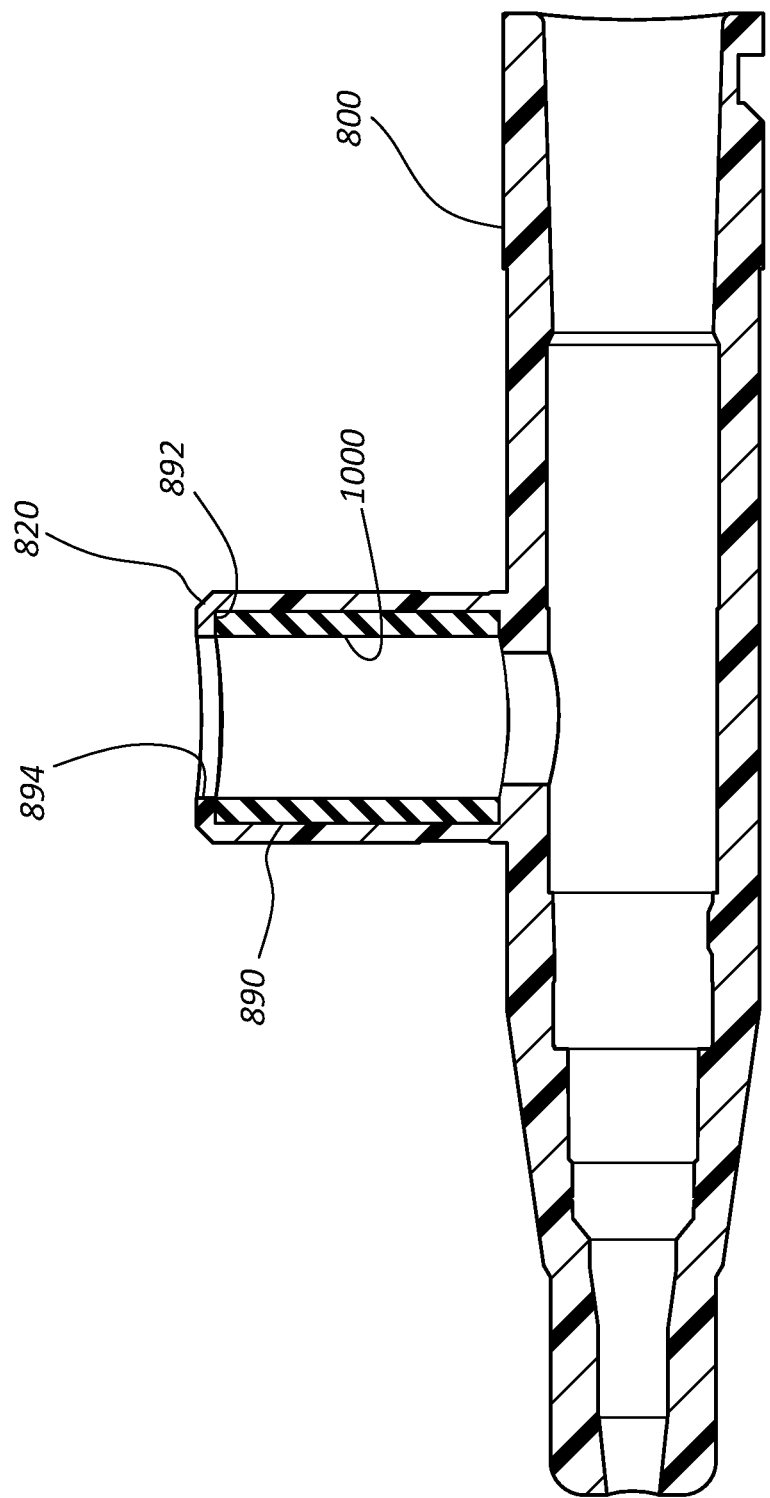
FIG. 10 illustrates a cross-sectional side view of a catheter adapter comprising a side port having an inner, annular recess into which is inserted an antimicrobial insert in accordance with a representative embodiment of the present invention.

In some instances, side port 820 of medical device 800 comprises an inner, annular recess 890 having a circumference configured to compatible receive an antimicrobial insert 1000, as shown in FIG. 10. In some instances, annular recess 890 further comprises heat stakes 894 that extend over a proximal end of antimicrobial insert 1000 to retain inert 1000 within side port 820.

Antimicrobial insert 1000 may comprise a polymer material having an antimicrobial agent configured to elute out of the polymer material when exposed to a fluid. Alternatively, antimicrobial insert 1000 may comprise a polymer material having an antimicrobial coating comprising an antimicrobial agent, wherein the antimicrobial agent is configured to elute out of the coating material when exposed to a fluid. Further, in some embodiments antimicrobial insert 1000 comprises a polymer material having an antimicrobial agent interspersed therein, and further comprises an antimicrobial coating having an antimicrobial agent dispersed therein, wherein the antimicrobial agents are configured to elute out of their respective carriers when exposed to a fluid.

Referring now to FIGS. 11A-11D, a method for forming an antimicrobial insert 1110 within a female luer connector 1102 is shown. Some embodiments of the present invention provide a female luer connector 1102 having a partially tapered inner surface 1120, wherein the proximal interior surface 1122 of inner surface 1120 is tapered, and the distal interior surface 1124 comprises parallel inner wall surfaces, i.e. no taper. Alternatively, distal interior surface 1124 may comprise a reduced taper. Distal interior surface 1124 further comprises an injection port 1130 having an outer opening 1132 and an inner opening 1134, wherein outer opening 1132 is in fluid communication with the interior of distal end 1124 via inner opening 1134. In some embodiments, distal interior surface 1124 further comprises a venting port 1140, as shown and discussed in connection with FIG. 11C.

Antimicrobial insert 1110 is formed within distal interior surface 1124 by injecting an antimicrobial material 1170 into the interior of luer connector 1102 via injection port 1130. Prior to injection of antimicrobial material 1170, a mandrel 1180 is inserted within the interior of female luer connector 1102. Mandrel 1180 comprises a tapered outer surface 1182 having an taper angle θ that is equal to the taper angle θ of proximal interior surface 1122, commonly referred to as the "luer taper".

Figure 11A:
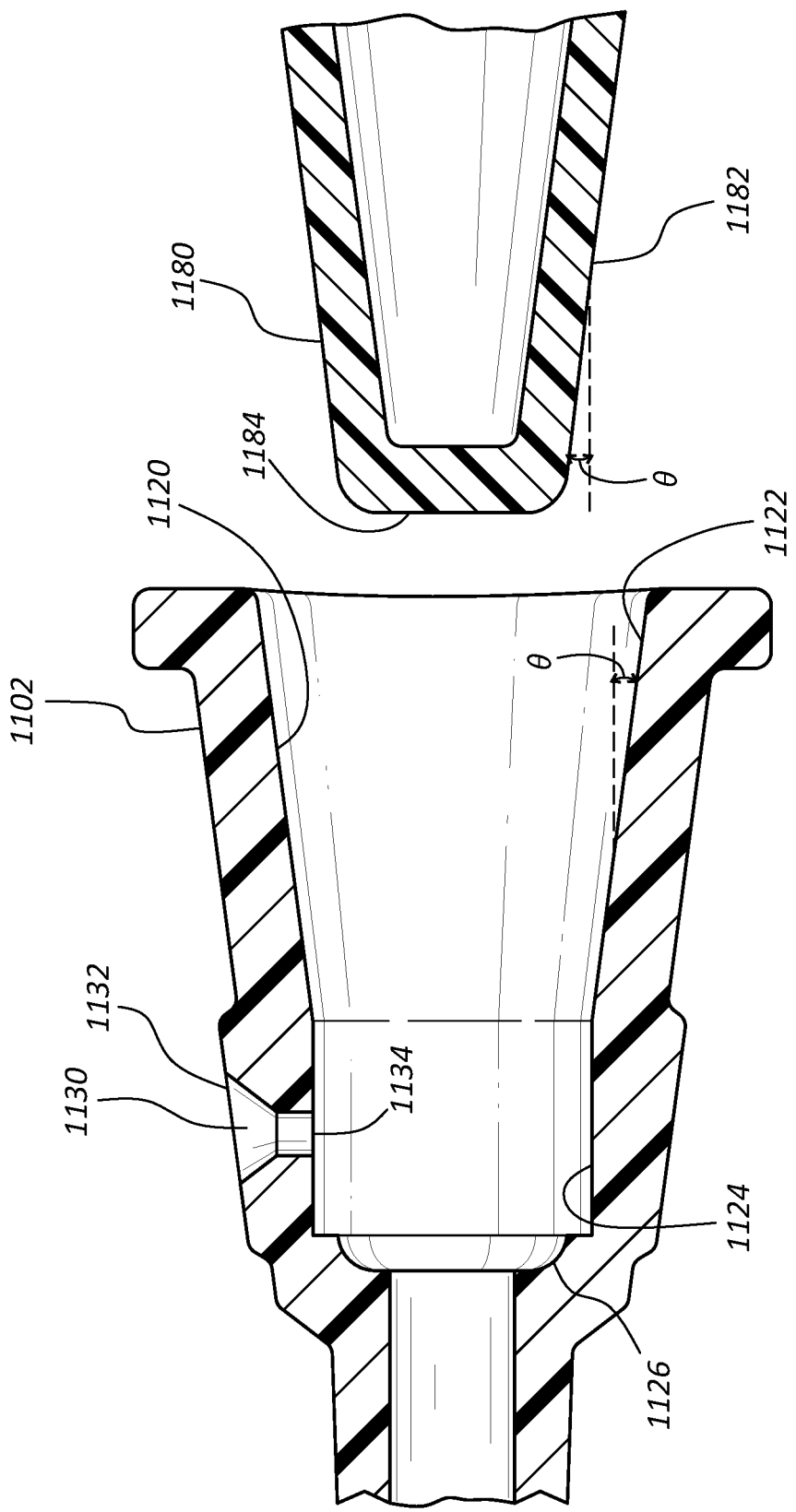
FIG. 11A illustrates a cross-sectional side view of a female luer port having at least one injection port for receiving an antimicrobial material, further demonstrating a method for injecting the antimicrobial material to form an antimicrobial coating on an inner surface of the female luer port in accordance with a representative embodiment of the present invention.
Figure 11B:
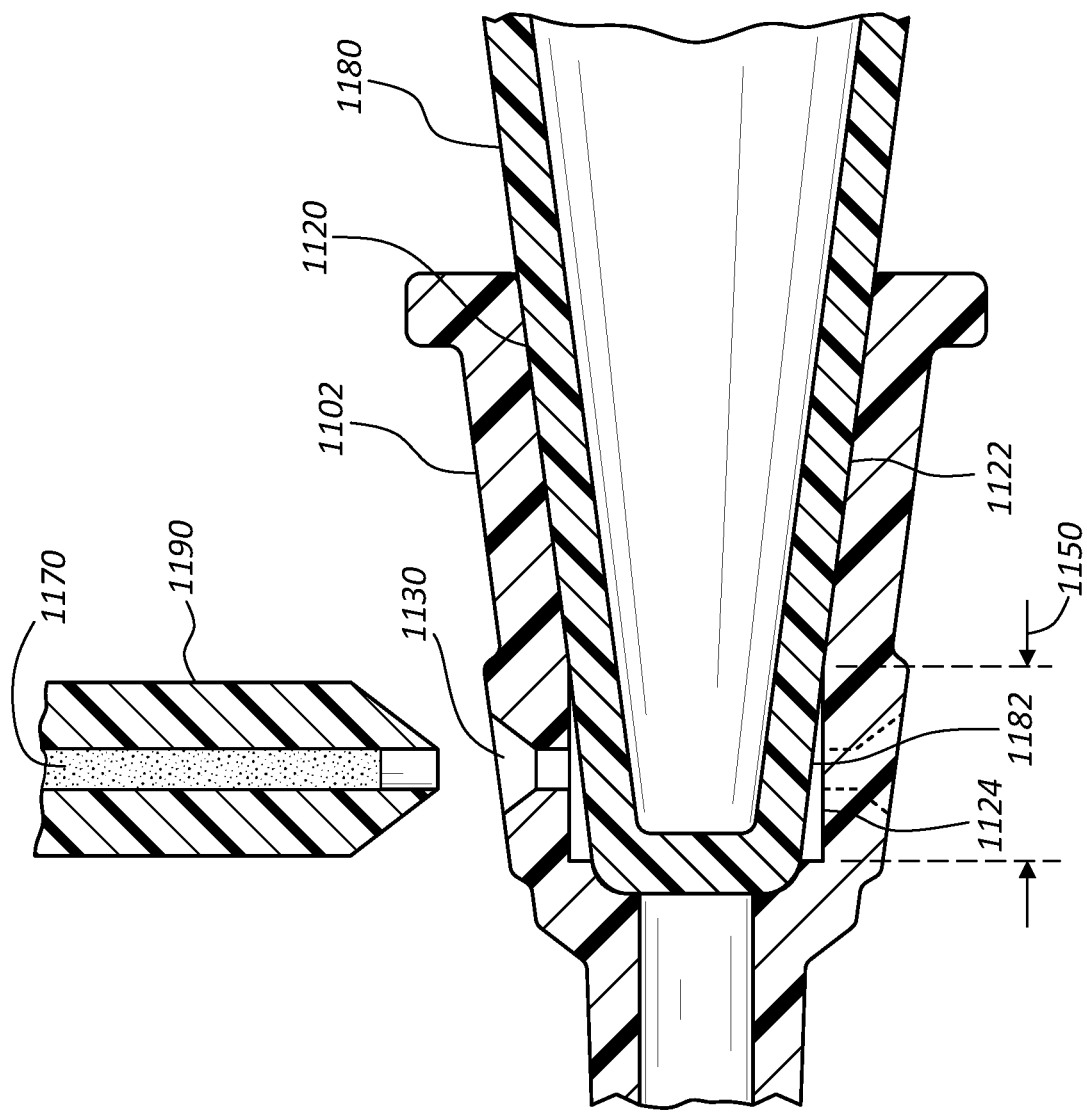
FIG. 11B illustrates a cross-sectional side view of the female luer port having at least one injection port for receiving the antimicrobial material, further demonstrating the method for injecting the antimicrobial material to form the antimicrobial coating on the inner surface of the female luer port in accordance with a representative embodiment of the present invention.

Mandrel 1180 is inserted into the interior of luer connector 1102 until the distal end 1184 of mandrel 1180 contacts the distal end surface 1126 of luer connector 1102, as shown in FIG. 11B. In some embodiments, the length 1140 of distal interior surface 1124, and the angle of luer taper e are selected so that outer surface 1182 fully contacts proximal interior surface 1122 when distal end 1184 contacts distal end surface 1126. Distal end surface 1126 and distal end 1184 are further configured to have mating surfaces, thereby forming a sealed interface when the two surfaces are in contact. Luer taper e of proximal interior surface 1122 and outer surface 1182 further form a sealed interface when the two surfaces are in contact.

Figure 11C:
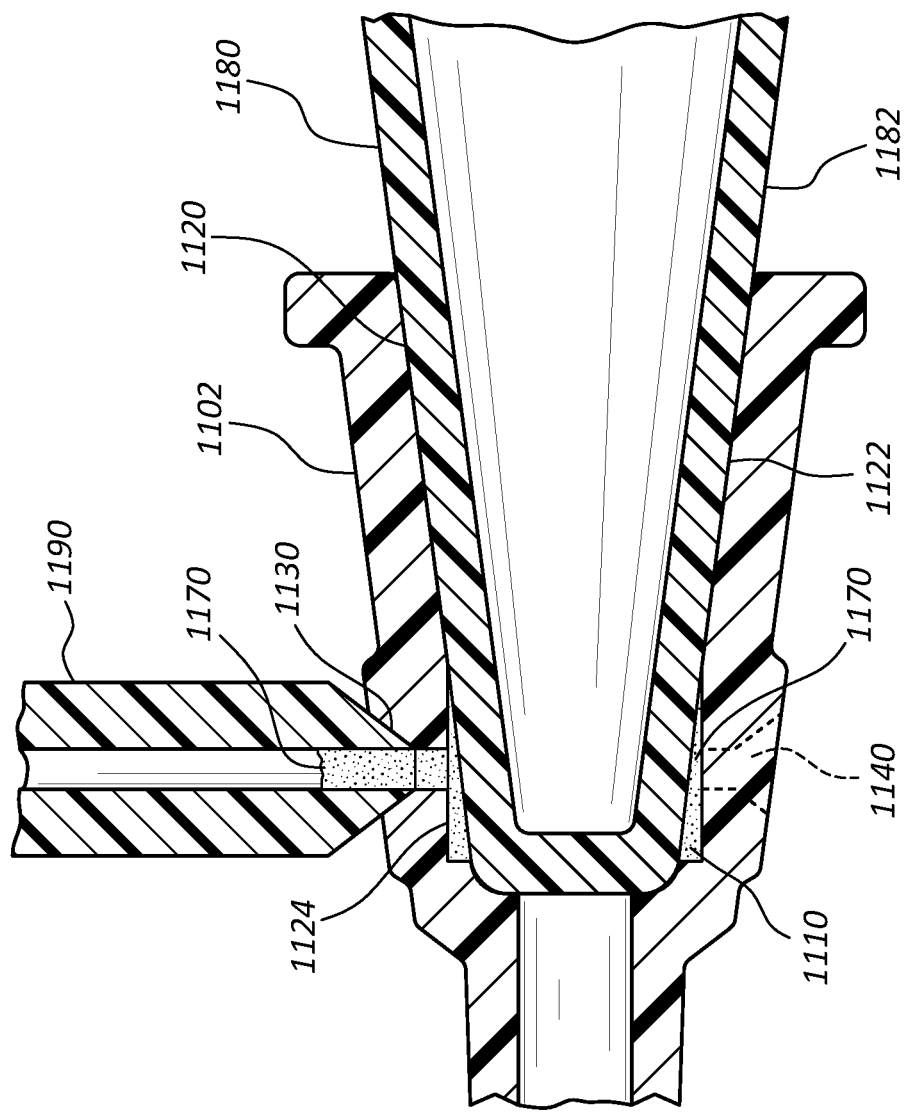
FIG. 11C illustrates a cross-sectional side view of the female luer port having at least one injection port for receiving the antimicrobial material, further demonstrating the method for injecting the antimicrobial material to form the antimicrobial coating on the inner surface of the female luer port in accordance with a representative embodiment of the present invention.

When mandrel 1180 is fully inserted within luer connector 1102, a wedge-shaped gap is formed between outer surface 1182 of mandrel 1180 and the parallel wall surfaces of distal interior surface 1124, as shown in FIG. 11C. Antimicrobial insert 1110 is formed within the wedge-shaped gap as antimicrobial material 1170 is injected therein via injection port 1130, such as by a syringe 1190. Alternatively, injection port 1130 may be accessed via automated injection machinery.

In some embodiments, luer connector 1102 further comprises a venting port 1140 that is positioned within distal interior surface 1124, approximately opposite injection port 1130. Venting port 1140 provides for the release of air and excess antimicrobial material 1170 from distal interior surface 1124 (i.e. the wedge-shaped gap) during the injection process. In some embodiments, luer connector 1102 comprises a plurality of injection ports. Luer connector 1102 may further comprise a plurality of venting ports.

Figure 11D:
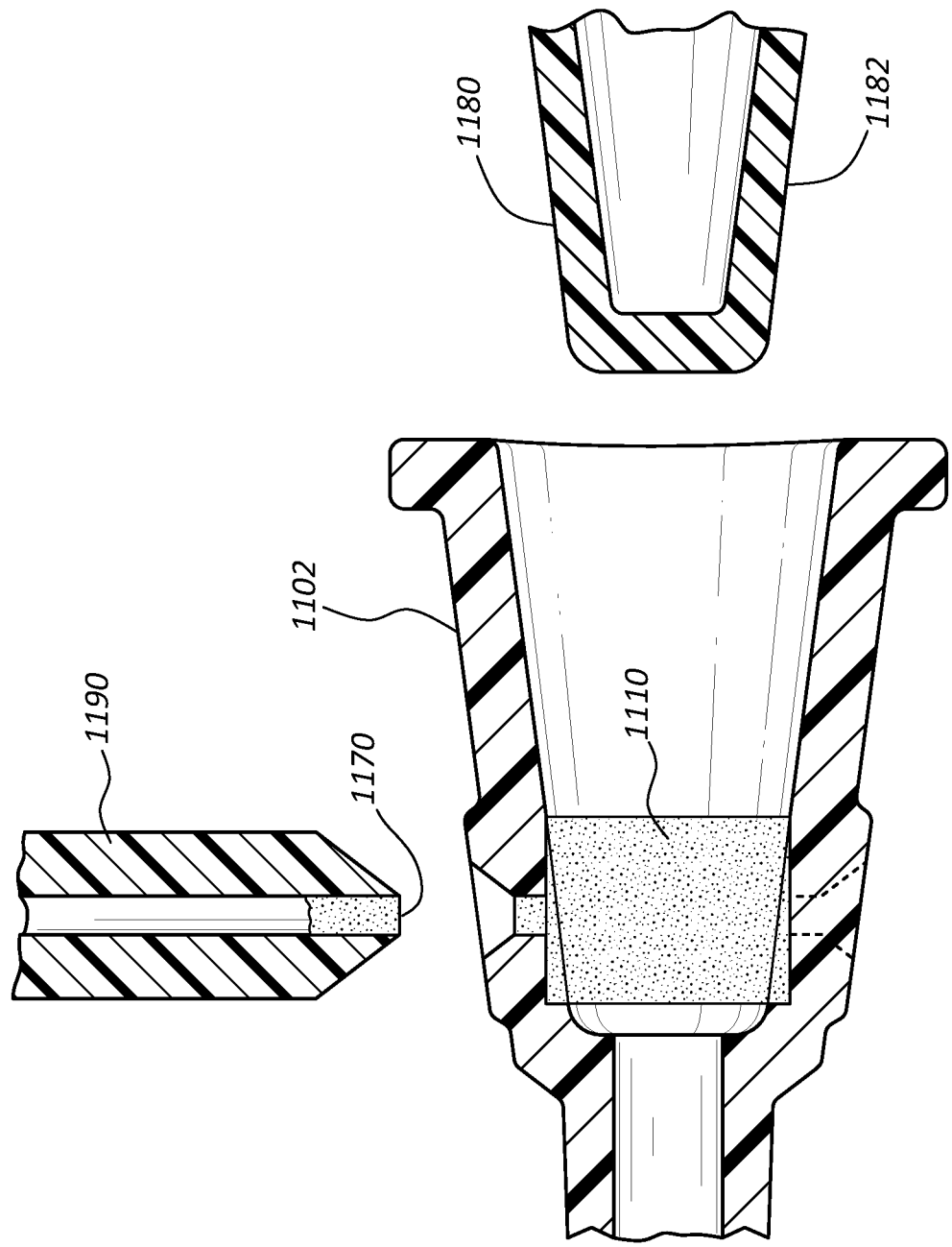
FIG. 11D illustrates a cross-sectional side view of the female luer port having at least one injection port for receiving the antimicrobial material, further demonstrating the method for injecting the antimicrobial material to form the antimicrobial coating on the inner surface of the female luer port in accordance with a representative embodiment of the present invention.

Mandrel 1180 remains positioned within luer connector 1102 until antimicrobial material 1170 is cured. In some instances, a releasing or non-stick agent is applied to outer surface 1182 prior to insertion of mandrel 1180 within luer connector 1102. The releasing agent is provided to prevent adhesion between the cured antimicrobial material 1170 and outer surface 1182. Once cured, mandrel 1170 is removed from luer connector 1102 and antimicrobial insert 1110 remains within distal interior surface 1124, as shown in FIG. 11D.

The method described above may alternatively be used to apply an antimicrobial material onto the outer surface of an internal (i.e. male) fluid fitting. For example, antimicrobial material may be injected through a hole on the inner surface of the fluid fitting to fill a recess or gap on the outer surface of the fluid fitting. Prior to the injection of the antimicrobial material, the fitting would be seated into tooling to control the shape of the injected antimicrobial material.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for forming an insert within a medical device, the method comprising:
    providing a medical device having a partially tapered inner surface, wherein a distal portion of the partially tapered inner surface comprises interior walls that are parallel;
    inserting a tapered mandrel into an interior of the medical device, the tapered mandrel having a luer taper that is approximately equal to a luer taper of a tapered portion of the partially tapered inner surface, an outer surface of the tapered mandrel forming a sealed interface with the tapered portion of the partially tapered inner surface, a distal end of the tapered mandrel forming a sealed interface with a distal end surface of the distal portion of the partially tapered inner surface, wherein a wedge-shaped gap is provided between the outer surface of the tapered mandrel and the parallel interior walls of the partially tapered inner surface;
    injecting an antimicrobial material into the wedge-shaped gap;
    curing the antimicrobial material; and
    remove the tapered mandrel.

2. The method of claim 1, wherein the base material matrix is cured using one of: UV curing, heat curing, or heat forming.

3. The method of claim 1, further comprising a step for providing an injection port though a wall surface of the medical device, wherein the injection port is in fluid communication with the wedge-shaped gap.

4. The method of claim 1, further comprising:
    coating the outer surface of the tapered mandrel with a releasing agent prior to inserting the tapered mandrel within the interior of the medical device.

* * * * *